United States Patent [19]

Judd et al.

[11] Patent Number: 5,616,327
[45] Date of Patent: Apr. 1, 1997

[54] M-PROTEIN PEPTIDES OF INFLUENZA VIRUS AS ANTIVIRAL AGENTS

[75] Inventors: Amrit K. Judd, Belmont, Calif.; Doris J. Bucher, New York, N.Y.

[73] Assignees: SRI International, Menlo Park, Calif.; New York Medical College, Valhalla, N.Y.

[21] Appl. No.: 335,303

[22] Filed: Nov. 7, 1994

Related U.S. Application Data

[63] Continuation of Ser. No. 821,031, Jan. 16, 1992, abandoned, which is a continuation-in-part of Ser. No. 717,429, Jun. 19, 1991, abandoned.

[51] Int. Cl.⁶ .................. A61K 39/385; A61K 38/10; A61K 9/127; C07K 17/02
[52] U.S. Cl. .......... 424/206.1; 424/450; 530/326; 530/335; 530/345; 530/400; 530/404; 530/405; 530/408; 530/409; 514/13; 514/14
[58] Field of Search ................ 530/326, 345, 530/400, 404, 405, 408, 409, 335; 424/450, 206.1; 514/13, 14

[56] References Cited

U.S. PATENT DOCUMENTS

| | | | |
|---|---|---|---|
| 4,981,782 | 1/1991 | Judd et al. | 435/5 |
| 5,019,383 | 5/1991 | Hopp | 424/88 |
| 5,039,522 | 8/1991 | Neurath | 424/89 |
| 5,136,019 | 8/1992 | Judd et al. | 530/326 |

OTHER PUBLICATIONS

Dailey et al (1977) J. Immunol 118(3):957–962.
Metzer et al (1989) Chem. Peptide Proteins 4:263–8.
Wiesmuller et al (1990) Peptides, 1990, Proc. Eur. Symp. 21st, Meeting Date 1990 Pub 1991 pp. 857–859.
Deres et al (1989) Nature 342:561–564.
Sehnke et al (1989) Virology 168:48–56.
Barbosa et al (1989) J. Virology 63(3):1404–1407.
Baylor et al (1988) "Transient Expression and Sequence of the Matrix (M1) Gene of WSN Influenza A virus in a Vaccinia Vector" Virology 163:618–621.

(List continued on next page.)

*Primary Examiner*—Kay K. A. Kim
*Attorney, Agent, or Firm*—Morrison & Foerster

[57] ABSTRACT

Peptides substantially corresponding to the 148–162 region of type A influenza M protein and additionally containing at least one amino acid in the 163–166 region are disclosed to have high activity as influenza transcription inhibitors and thus as antiviral agents against influenza virus and other RNA viruses. The modification of these peptides by incorporation into liposomes or by addition of long-chain alkylamino acids is also shown as in the use of all such materials in antiviral drug formulations.

14 Claims, 1 Drawing Sheet

OTHER PUBLICATIONS

Maikushin et al (1988) "Nucleotide seq. of RNA Segment 7 and the predicted amino sequence of M1 and M2 proteins . . . influenza virus" Virus Res 10:263–272.

Cox et al (1988) "Identification of Sequence Changes . . . Influenza Virus . . . " Virology 167:554–567.

Buckler–White et al (1986) "Characterization of a Gene Coding for M protein" J. Virology 57(2):670–700.

Judd et al., *Chem. Abstr.* Abstract No. 229398f, (1991).

M.W. Khan, M. Gallagher, D. Bucher, C.P. Cerini, and E.D. Kilbourne. *J. Clin. Microbiol.* 16(1):115–122 (1982).

A.Y. Zvonarjev and Y.Z. Ghendon. *J. Virol.* 33(2):583–586 (1980).

Z. Ye, R. Pal, J.W. Fox, and R.R. Wagner. *J. Virol.* 61(2):239–246 (1987).

R.W. Hankins, K. Nagata, D.J. Bucher, S. Popple, and A. Ishihama. *Virus Genes* 3(2):111–126 (1989).

Z. Ye, N.W. Baylor, and R.R. Wagner. *J. Virol.* 63(9):3586–3594 (1989).

D. Bucher, S. Popple, M. Baer, A. Mikhail, Y.–F. Gong, C. Whiteker, E. Paoletti, and A. Judd. *J. Virol.* 63(9):3622–3633 (1989).

G. Winter and S. Fields. *Nucleic Acids Res.* 8(9):1965–1974 (1980).

R.A. Lamb and C.J. Lai. *Virology* 112:746–751 (1981).

J.A. Huddleston and G.G. Brownlee. *Nucleic Acids Res.* 10(3):1029–1038 (1982).

D.J. Bucher. The Negative Strand Viruses. B.W.J. Mahy and R.D. Barry (eds.), vol. I, Academic Press, 1975, Chapter 9, pp. 133–143.

D.J. Bucher, S.S.–L. Li, J.M. Kehoe, and E.D. Kilbourne, *Proc. Natl. Acad. Sci. USA* 73(1):238–242 (1976).

D.J. Bucher. *Biochim. Biophys. Acta* 483:393–399 (1977).

M. Gallagher, D.J. Bucher, R. Dourmashkin, J.F. Davis, G. Rosenn, and E.D. Kilbourne. *J. Clin. Microbiol.* 20(1):89–93 (1984).

M.W. Kahn, D.J. Bucher, A.K. Koul, G. Kalish, and E.D. Kilbourne, *J. Clin. Microbiol.* 16(5):813–820 (1982).

D.J. Bucher, I.G. Kharitonenkov, M.W. Khan, A. Palo, D. Holloway, and A. Mikhail. *J. Immunol. Methods* 96:77–85 (1987).

D. Bucher, A. Mikhail. S. Popple, M. Baer, and C. Whitaker, VIIth International Congress of Virology, Edmonton, Canada, Abstract, R23.28.

O.M. Rochovansky. *Virology* 73, 327–338 (1976).

J.J. Plotch, M. Bouloy, I. Ulmann, and R.M. Krug. *Cell* 23:847–858 (1981).

A. Kato, K. Mizumoto, and A. Ishihama, *Virus Res.* 3: 115–127 (1985).

R.G. Almquist, W.–R. Chao, A.K. Judd, C. Mitoma, D.J. Rossi, R.E. Panasevich, and R.J. Matthews, *J. Med. Chem.* 31:561–567 (1988).

J.M. Stewart and J.D. Young. In Solid Phase Peptide Synthesis. J.M. Stewart and J.D. Young (eds.). Pierce Chemical Co., 1984, p. 83.

S.L. Harbeson and D.H. Rich. *J. Med. Chem.* 32:1378–1392 (1989).

M.T. Garcia–Lopez, R. Gonzalez–Muniz, and J.R. Harto. *Tetrahedron* 44(16):5131–5138 (1988).

M.T. Garcia–Lopez, R. Gonzalez–Muniz, and J.R. Harto. *Tetrahedron Lett.* 29(13):1577–1580 (1988).

R.L. Johnson and R.B. Miller. *Int. J. Peptide Protein Res.* 23, 581–590 (1984).

J.V.N.V. Prasad and D.H. Rich. *Tetrahedron Lett.* 31(13):1803–1806 (1990).

B.E. Evans, K.E. Rittle, C.F. Homnick, J.P. Springer, J. Hirshfield, and D.F. Veber. *J. Org. Chem.* 50:4615–4625 (1985).

A.H. Fray, R.L. Kaye, and E.F. Kleinman. *J. Org. Chem.* 51:4828–4833 (1986).

K. Deres, H. Schlid, K.–H., Weismüller, G. Jung, and H.–G. Rammensee. *Nature* 342:561–564 (1989).

I. Toth, R.A. Hughes, M.R. Munday, P. Mascagni, and W.A. Gibbons. Proceedings of the Eleventh American Peptide Symposium. J.E. Rivier and G.R. Marshall (eds.), ESCOM, Leiden, pp. 1078–1079 (1990).

Y. Sanchez, I. Ionescu–Matiu, G.R. Dreesman, W. Kramp, H.R. Six, F.B. Hollinger, and J.L. Melnick, *Infect. Immun.* 30(3):728–733 (1980).

G.W. Both and G.M. Air. *Eur. J. Biochem.* 96:363–372 (1970).

B.E. Johansson, D.J. Bucher, and E.D. Kilbourne. *J. Virol.* 63(3):1239–1246 (1989).

A. Gregorriades. *Virology* 79:449–454 (1977).

National Academy of Sciences. New vaccine development. Establishing priorities. Vol. I. Diseases of Importance in the United States, Washington, D.C., National Academy Press, Appendix K, Prospects for immunizing against influenza viruses A and B (1985) pp. 342–364.

Advisory Committee on Immunization Practices (ACIP). *Morbidity and Mortality Weekly Report (MMWR)* 35(20):317–331 (1986).

R. Dolin and D.W. Bentley. Options for the Control of Influenza. A.P. Kenda and P.A. Patriarca (eds.). Alan R. Liss, Inc., New York 1986, pp. 317–326.

Centers for Disease Control (CDC). Influenza–United States, 1985–1986 season. *Morbidity and Morality Weekly Report (MMWR)* 35(29):470–479 (1986).

I.T. Schulze. *Virology* 42:890–904 (1970).

D.J. Bucher, I.G. Kharitonenkov, J.A. Zakomirdin, V.B. Gregoriev, S.M. Klimenko, and J.F. Davis. *J. Virol.* 36(2):586–590 (1980).

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Cys Ala Thr Cys Glu Gln Ile Ala Asp Ser Gln His Arg Ser His Arg
1               5                   10                  15
Gln Met Val
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 15
        ( D ) OTHER INFORMATION: /note="Zinc-binding residue"

( x i ) SEQUENCE DESCRIPTION: SEQ ID NO:2:

```
Cys Ala Thr Cys Glu Gln Ile Ala Asp Ser Gln His Arg Ser His Arg
1               5                   10                  15
Gln Met Val
```

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:

(A) NAME/KEY: Modified-site
                (B) LOCATION: 4
                (D) OTHER INFORMATION: /note="Zinc-binding residue"

(ix) FEATURE:
                (A) NAME/KEY: Modified-site
                (B) LOCATION: 12
                (D) OTHER INFORMATION: /note="Zinc-binding residue"

(ix) FEATURE:
                (A) NAME/KEY: Modified-site
                (B) LOCATION: 15
                (D) OTHER INFORMATION: /note="Zinc-binding residue"

(xi) SEQUENCE DESCRIPTION: SEQ ID NO:3:

Cys Ala Thr Cys Glu Gln Ile Ala Asp Ser Gln His Arg Ser His Arg
1               5                   10                  15

Gln Met (2) INFORMATION FOR SEQ ID NO:4:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note="Zinc-binding residue"

(ix) FEATURE:
            (A) NAME/KEY: Modified-site
            (B) LOCATION: 4
            (D) OTHER INFORMATION: /note="Zinc-binding residue"

(ix) FEATURE:
            (A) NAME/KEY: Modified-site
            (B) LOCATION: 12
            (D) OTHER INFORMATION: /note="Zinc-binding residue"

(ix) FEATURE:
            (A) NAME/KEY: Modified-site
            (B) LOCATION: 15
            (D) OTHER INFORMATION: /note="Zinc-binding residue"

(xi) SEQUENCE DESCRIPTION: SEQ ID NO:4:

Cys Ala Thr Cys Glu Gln Ile Ala Asp Ser Gln His Arg Ser His Arg
1               5                   10                  15

Gln (2) INFORMATION FOR SEQ ID NO:5:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note="Zinc-binding residue"

(ix) FEATURE:
            (A) NAME/KEY: Modified-site
            (B) LOCATION: 4
            (D) OTHER INFORMATION: /note="Zinc-binding residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 15
    ( D ) OTHER INFORMATION: /note="Zinc-binding residue"

( x i ) SEQUENCE DESCRIPTION: SEQ ID NO:5:

```
Cys Ala Thr Cys Glu Gln Ile Ala Asp Ser Gln His Arg Ser His Arg
1               5                   10                  15
```

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 15
        ( D ) OTHER INFORMATION: /note="Zinc-binding residue"

( x i ) SEQUENCE DESCRIPTION: SEQ ID NO:6:

```
Cys Ala Thr Cys Glu Gln Ile Ala Asp Ser Gln His Arg Ser His
1               5                   10                  15
```

( 2 ) INFORMATION FOR SEQ ID NO:7:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 11
        ( D ) OTHER INFORMATION: /note="Zinc-binding residue"

( i x ) FEATURE:
        ( A ) NAME/KEY: Modified-site
        ( B ) LOCATION: 14

(D) OTHER INFORMATION: /note="Zinc-binding residue"

(xi) SEQUENCE DESCRIPTION: SEQ ID NO:7:

Cys Ala Thr Cys Gln Ile Ala Asp Ser Gln His Arg Ser His Arg Gln
1               5                   10                  15
Met Val (2) INFORMATION FOR SEQ ID NO:8:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Zinc-binding residue"

(ix) FEATURE:
        (A) NAME/KEY: Modified-site
        (B) LOCATION: 4
        (D) OTHER INFORMATION: /note="Zinc-binding residue"

(ix) FEATURE:
        (A) NAME/KEY: Modified-site
        (B) LOCATION: 10
        (D) OTHER INFORMATION: /note="Zinc-binding residue"

(ix) FEATURE:
        (A) NAME/KEY: Modified-site
        (B) LOCATION: 13
        (D) OTHER INFORMATION: /note="Zinc-binding residue"

(xi) SEQUENCE DESCRIPTION: SEQ ID NO:8:

Cys Ala Thr Cys Ile Ala Asp Ser Gln His Arg Ser His Arg Gln Met
1               5                   10                  15
Val (2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Zinc-binding residue"

(ix) FEATURE:
        (A) NAME/KEY: Modified-site
        (B) LOCATION: 4
        (D) OTHER INFORMATION: /note="Zinc-binding residue"

(ix) FEATURE:
        (A) NAME/KEY: Modified-site
        (B) LOCATION: 9
        (D) OTHER INFORMATION: /note="Zinc-binding residue"

(ix) FEATURE:
        (A) NAME/KEY: Modified-site
        (B) LOCATION: 12
        (D) OTHER INFORMATION: /note="Zinc-binding residue"

(xi) SEQUENCE DESCRIPTION: SEQ ID NO:9:

Cys Ala Thr Cys Ala Asp Ser Gln His Arg Ser His Arg Gln Met Val
1               5                   10                  15

( 2 ) INFORMATION FOR SEQ ID NO:10:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 3
        ( D ) OTHER INFORMATION: /note="Zinc-binding residue"

( i x ) FEATURE:
        ( A ) NAME/KEY: Modified-site
        ( B ) LOCATION: 11
        ( D ) OTHER INFORMATION: /note="Zinc-binding residue"

( i x ) FEATURE:
        ( A ) NAME/KEY: Modified-site
        ( B ) LOCATION: 14
        ( D ) OTHER INFORMATION: /note="Zinc-binding residue"

( x i ) SEQUENCE DESCRIPTION: SEQ ID NO:10:

Cys Thr Cys Glu Gln Ile Ala Asp Ser Gln His Arg Ser His Arg Gln
1               5                   10                  15

Met Val ( 2 ) INFORMATION FOR SEQ ID NO:11:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 3
        ( D ) OTHER INFORMATION: /note="Zinc-binding residue"

( i x ) FEATURE:
        ( A ) NAME/KEY: Modified-site
        ( B ) LOCATION: 11
        ( D ) OTHER INFORMATION: /note="Zinc-binding residue"

( i x ) FEATURE:
        ( A ) NAME/KEY: Modified-site
        ( B ) LOCATION: 14
        ( D ) OTHER INFORMATION: /note="Zinc-binding residue"

( x i ) SEQUENCE DESCRIPTION: SEQ ID NO:11:

Cys Ala Cys Glu Gln Ile Ala Asp Ser Gln His Arg Ser His Arg Gln
1               5                   10                  15

Met Val ( 2 ) INFORMATION FOR SEQ ID NO:12:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Zinc-binding residue"

( i x ) FEATURE:
    ( A ) NAME/KEY: Modified-site
    ( B ) LOCATION: 4
    ( D ) OTHER INFORMATION: /note="Zinc-binding residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 14
    ( D ) OTHER INFORMATION: /note="Zinc-binding residue"

( x i ) SEQUENCE DESCRIPTION: SEQ ID NO:12:

Cys Ala Thr Cys Glu Gln Ile Ala Asp Ser Gln His Arg His Arg Gln
1               5                   10                  15

Met Val ( 2 ) INFORMATION FOR SEQ ID NO:13:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Zinc-binding residue"

( i x ) FEATURE:
    ( A ) NAME/KEY: Modified-site
    ( B ) LOCATION: 4
    ( D ) OTHER INFORMATION: /note="Zinc-binding residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 14
    ( D ) OTHER INFORMATION: /note="Zinc-binding residue"

( x i ) SEQUENCE DESCRIPTION: SEQ ID NO:13:

Cys Ala Thr Cys Glu Gln Ile Ala Asp Ser Gln His Arg His Arg Gln
1               5                   10                  15

Met Val ( 2 ) INFORMATION FOR SEQ ID NO:14:

( i ) SEQUENCE CHARACTERISTICS:
    ( A ) LENGTH: 19 amino acids (B) TYPE: amino acid
(C) STRANDEDNESS: single
(D) TOPOLOGY: linear (ii) MOLECULE TYPE: peptide (ix) FEATURE:
  (A) NAME/KEY: Modified-site
  (B) LOCATION: 1
  (D) OTHER INFORMATION: /label=Ac- (ix) FEATURE:
  (A) NAME/KEY: Modified-site
  (B) LOCATION: 1
  (D) OTHER INFORMATION: /note="Zinc-binding residue"

(ix) FEATURE:
  (A) NAME/KEY: Modified-site
  (B) LOCATION: 4
  (D) OTHER INFORMATION: /note="Zinc-binding residue"

(ix) FEATURE:
  (A) NAME/KEY: Modified-site
  (B) LOCATION: 12
  (D) OTHER INFORMATION: /note="Zinc-binding residue"

(ix) FEATURE:
  (A) NAME/KEY: Modified-site
  (B) LOCATION: 15
  (D) OTHER INFORMATION: /note="Zinc-binding residue"

(xi) SEQUENCE DESCRIPTION: SEQ ID NO:14:

```
Cys Ala Thr Cys Glu Gln Ile Ala Asp Ser Gln His Arg Ser His Arg
1               5                   10                  15

Gln Met Val
```

(2) INFORMATION FOR SEQ ID NO:15:

(i) SEQUENCE CHARACTERISTICS:
  (A) LENGTH: 19 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Modified-site
  (B) LOCATION: 1
  (D) OTHER INFORMATION: /label=Ac- (ix) FEATURE:
  (A) NAME/KEY: Modified-site
  (B) LOCATION: 1
  (D) OTHER INFORMATION: /note="Zinc-binding residue"

(ix) FEATURE:
  (A) NAME/KEY: Modified-site
  (B) LOCATION: 4
  (D) OTHER INFORMATION: /note="Zinc-binding residue"

(ix) FEATURE:
  (A) NAME/KEY: Modified-site
  (B) LOCATION: 12
  (D) OTHER INFORMATION: /note="Zinc-binding residue"

(ix) FEATURE:
  (A) NAME/KEY: Modified-site
  (B) LOCATION: 15
  (D) OTHER INFORMATION: /note="Zinc-binding residue"

(ix) FEATURE:
  (A) NAME/KEY: Modified-site
  (B) LOCATION: 19
  (D) OTHER INFORMATION: /label=NH2

(xi) SEQUENCE DESCRIPTION: SEQ ID NO:15:

```
Cys Ala Thr Cys Glu Gln Ile Ala Asp Ser Gln His Arg Ser His Arg
1               5                   10                  15

Gln Met Val
```

(2) INFORMATION FOR SEQ ID NO:16:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note="Replacement residue"

(ix) FEATURE:
        (A) NAME/KEY: Modified-site
        (B) LOCATION: 1
        (D) OTHER INFORMATION: /note="Zinc-binding residue"

(ix) FEATURE:
        (A) NAME/KEY: Modified-site
        (B) LOCATION: 4
        (D) OTHER INFORMATION: /note="Zinc-binding residue"

(ix) FEATURE:
        (A) NAME/KEY: Modified-site
        (B) LOCATION: 12
        (D) OTHER INFORMATION: /note="Zinc-binding residue"

(ix) FEATURE:
        (A) NAME/KEY: Modified-site
        (B) LOCATION: 15
        (D) OTHER INFORMATION: /note="Zinc-binding residue"

(xi) SEQUENCE DESCRIPTION: SEQ ID NO:16:

```
Cys Ala Ala Cys Glu Gln Ile Ala Asp Ser Gln His Arg Ser His Arg
1               5                   10                  15

Gln Met Val
```

(2) INFORMATION FOR SEQ ID NO:17:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /note="Replacement residue"

(ix) FEATURE:
        (A) NAME/KEY: Modified-site
        (B) LOCATION: 1
        (D) OTHER INFORMATION: /note="Zinc-binding residue"

(ix) FEATURE:
        (A) NAME/KEY: Modified-site
        (B) LOCATION: 4
        (D) OTHER INFORMATION: /note="Zinc-binding residue"

(ix) FEATURE:
        (A) NAME/KEY: Modified-site
        (B) LOCATION: 12
        (D) OTHER INFORMATION: /note="Zinc-binding residue"

( i x ) FEATURE:
    ( A ) NAME/KEY: Modified-site
    ( B ) LOCATION: 15
    ( D ) OTHER INFORMATION: /note="Zinc-binding residue"

( x i ) SEQUENCE DESCRIPTION: SEQ ID NO:17:

```
Cys Ala Thr Cys Ala Gln Ile Ala Asp Ser Gln His Arg Ser His Arg
1               5                   10                  15

Gln Met Val
```

( 2 ) INFORMATION FOR SEQ ID NO:18:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION: 6
    ( D ) OTHER INFORMATION: /note="Replacement residue"

( i x ) FEATURE:
    ( A ) NAME/KEY: Modified-site
    ( B ) LOCATION: 1
    ( D ) OTHER INFORMATION: /note="Zinc-binding residue"

( i x ) FEATURE:
    ( A ) NAME/KEY: Modified-site
    ( B ) LOCATION: 4
    ( D ) OTHER INFORMATION: /note="Zinc-binding residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 15
    ( D ) OTHER INFORMATION: /note="Zinc-binding residue"

( x i ) SEQUENCE DESCRIPTION: SEQ ID NO:18:

```
Cys Ala Thr Cys Glu Ala Ile Ala Asp Ser Gln His Arg Ser His Arg
1               5                   10                  15

Gln Met Val
```

( 2 ) INFORMATION FOR SEQ ID NO:19:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION: 7
    ( D ) OTHER INFORMATION: /note="Replacement residue"

( i x ) FEATURE:
    ( A ) NAME/KEY: Modified-site
    ( B ) LOCATION: 1
    ( D ) OTHER INFORMATION: /note="Zinc-binding residue"

( i x ) FEATURE:
    ( A ) NAME/KEY: Modified-site
    ( B ) LOCATION: 4
    ( D ) OTHER INFORMATION: /note="Zinc-binding residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 15
        ( D ) OTHER INFORMATION: /note="Zinc-binding residue"

( x i ) SEQUENCE DESCRIPTION: SEQ ID NO:19:

Cys Ala Thr Cys Glu Gln Ala Ala Asp Ser Gln His Arg Ser His Arg
1               5                   10                  15

Gln Met Val ( 2 ) INFORMATION FOR SEQ ID NO:20:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 9
        ( D ) OTHER INFORMATION: /note="Replacement residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 15
        ( D ) OTHER INFORMATION: /note="Zinc-binding residue"

( x i ) SEQUENCE DESCRIPTION: SEQ ID NO:20:

Cys Ala Thr Cys Glu Gln Ile Ala Ala Ser Gln His Arg Ser His Arg
1               5                   10                  15

Gln Met Val ( 2 ) INFORMATION FOR SEQ ID NO:21:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4

( D ) OTHER INFORMATION: /note="Zinc-binding residue"

( i x ) FEATURE:
    ( A ) NAME/KEY: Modified-site
    ( B ) LOCATION: 10
    ( D ) OTHER INFORMATION: /note="Replacement residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 15
    ( D ) OTHER INFORMATION: /note="Zinc-binding residue"

( x i ) SEQUENCE DESCRIPTION: SEQ ID NO:21:

Cys Ala Thr Cys Glu Gln Ile Ala Asp Ala Gln His Arg Ser His Arg
1                   5                       10                  15

Gln Met Val ( 2 ) INFORMATION FOR SEQ ID NO:22:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 11
        ( D ) OTHER INFORMATION: /note="Replacement residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 15
        ( D ) OTHER INFORMATION: /note="Zinc-binding residue"

( x i ) SEQUENCE DESCRIPTION: SEQ ID NO:22:

Cys Ala Thr Cys Glu Gln Ile Ala Asp Ser Ala His Arg Ser His Arg
1                   5                       10                  15

Gln Met Val ( 2 ) INFORMATION FOR SEQ ID NO:23:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site (B) LOCATION: 1
(D) OTHER INFORMATION: /note="Zinc-binding residue"

(ix) FEATURE:
(A) NAME/KEY: Modified-site
(B) LOCATION: 4
(D) OTHER INFORMATION: /note="Zinc-binding residue"

(ix) FEATURE:
(A) NAME/KEY: Modified-site
(B) LOCATION: 12
(D) OTHER INFORMATION: /note="Zinc-binding residue"

(ix) FEATURE:
(A) NAME/KEY: Modified-site
(B) LOCATION: 15
(D) OTHER INFORMATION: /note="Zinc-binding residue"

(ix) FEATURE:
(A) NAME/KEY: Modified-site
(B) LOCATION: 13
(D) OTHER INFORMATION: /note="Replacement residue"

(xi) SEQUENCE DESCRIPTION: SEQ ID NO:23:

Cys Ala Thr Cys Glu Gln Ile Ala Asp Ser Gln His Ala Ser His Arg
1               5                   10                  15

Gln Met Val (2) INFORMATION FOR SEQ ID NO:24:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Zinc-binding residue"

(ix) FEATURE:
(A) NAME/KEY: Modified-site
(B) LOCATION: 4
(D) OTHER INFORMATION: /note="Zinc-binding residue"

(ix) FEATURE:
(A) NAME/KEY: Modified-site
(B) LOCATION: 12
(D) OTHER INFORMATION: /note="Zinc-binding residue"

(ix) FEATURE:
(A) NAME/KEY: Modified-site
(B) LOCATION: 15
(D) OTHER INFORMATION: /note="Zinc-binding residue"

(ix) FEATURE:
(A) NAME/KEY: Modified-site
(B) LOCATION: 14
(D) OTHER INFORMATION: /note="Replacement residue"

(xi) SEQUENCE DESCRIPTION: SEQ ID NO:24:

Cys Ala Thr Cys Glu Gln Ile Ala Asp Ser Gln His Arg Ala His Arg
1               5                   10                  15

Gln Met Val (2) INFORMATION FOR SEQ ID NO:25:

(i) SEQUENCE CHARACTERISTICS:
(A) LENGTH: 19 amino acids
(B) TYPE: amino acid
(C) STRANDEDNESS: single ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Zinc-binding residue"

( i x ) FEATURE:
    ( A ) NAME/KEY: Modified-site
    ( B ) LOCATION: 4
    ( D ) OTHER INFORMATION: /note="Zinc-binding residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 15
    ( D ) OTHER INFORMATION: /note="Zinc-binding residue"

( i x ) FEATURE:
    ( A ) NAME/KEY: Modified-site
    ( B ) LOCATION: 16
    ( D ) OTHER INFORMATION: /note="Replacement residue"

( x i ) SEQUENCE DESCRIPTION: SEQ ID NO:25:

Cys Ala Thr Cys Glu Gln Ile Ala Asp Ser Gln His Arg Ser His Ala
1               5                   10                  15

Gln Met Val ( 2 ) INFORMATION FOR SEQ ID NO:26:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Zinc-binding residue"

( i x ) FEATURE:
    ( A ) NAME/KEY: Modified-site
    ( B ) LOCATION: 4
    ( D ) OTHER INFORMATION: /note="Zinc-binding residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 15
    ( D ) OTHER INFORMATION: /note="Zinc-binding residue"

( i x ) FEATURE:
    ( A ) NAME/KEY: Modified-site
    ( B ) LOCATION: 17
    ( D ) OTHER INFORMATION: /note="Replacement residue"

( x i ) SEQUENCE DESCRIPTION: SEQ ID NO:26:

Cys Ala Thr Cys Glu Gln Ile Ala Asp Ser Gln His Arg Ser His Arg
1               5                   10                  15

Ala Met Val (2) INFORMATION FOR SEQ ID NO:27:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Zinc-binding residue"

(ix) FEATURE:
        (A) NAME/KEY: Modified-site
        (B) LOCATION: 4
        (D) OTHER INFORMATION: /note="Zinc-binding residue"

(ix) FEATURE:
        (A) NAME/KEY: Modified-site
        (B) LOCATION: 12
        (D) OTHER INFORMATION: /note="Zinc-binding residue"

(ix) FEATURE:
        (A) NAME/KEY: Modified-site
        (B) LOCATION: 15
        (D) OTHER INFORMATION: /note="Zinc-binding residue"

(ix) FEATURE:
        (A) NAME/KEY: Modified-site
        (B) LOCATION: 18
        (D) OTHER INFORMATION: /note="Replacement residue"

(xi) SEQUENCE DESCRIPTION: SEQ ID NO:27:

```
Cys  Ala  Thr  Cys  Glu  Gln  Ile  Ala  Asp  Ser  Gln  His  Arg  Ser  His  Arg
 1                  5                        10                       15
Gln  Ala  Val
```

(2) INFORMATION FOR SEQ ID NO:28:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Zinc-binding residue"

(ix) FEATURE:
        (A) NAME/KEY: Modified-site
        (B) LOCATION: 4
        (D) OTHER INFORMATION: /note="Zinc-binding residue"

(ix) FEATURE:
        (A) NAME/KEY: Modified-site
        (B) LOCATION: 12
        (D) OTHER INFORMATION: /note="Zinc-binding residue"

(ix) FEATURE:
        (A) NAME/KEY: Modified-site
        (B) LOCATION: 15
        (D) OTHER INFORMATION: /note="Zinc-binding residue"

(ix) FEATURE:
        (A) NAME/KEY: Modified-site
        (B) LOCATION: 19
        (D) OTHER INFORMATION: /note="Replacement residue"

(xi) SEQUENCE DESCRIPTION: SEQ ID NO:28:

Cys Ala Thr Cys Glu Gln Ile Ala Asp Ser Gln His Arg Ser His Arg
1               5                       10                      15

Gln Met Ala ( 2 ) INFORMATION FOR SEQ ID NO:29:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 13
        ( D ) OTHER INFORMATION: /note="Replacement residue"

( i x ) FEATURE:
        ( A ) NAME/KEY: Modified-site
        ( B ) LOCATION: 15
        ( D ) OTHER INFORMATION: /note="Zinc-binding residue"

( x i ) SEQUENCE DESCRIPTION: SEQ ID NO:29:

Cys Ala Thr Cys Glu Gln Ile Ala Asp Ser Gln His Lys Ser His Arg
1               5                       10                      15

Gln Met Val ( 2 ) INFORMATION FOR SEQ ID NO:30:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 15
        ( D ) OTHER INFORMATION: /note="Zinc-binding residue"

( i x ) FEATURE:

( A ) NAME/KEY: Modified-site
( B ) LOCATION: 16
( D ) OTHER INFORMATION: /note="Replacement residue"

( x i ) SEQUENCE DESCRIPTION: SEQ ID NO:30:

Cys Ala Thr Cys Glu Gln Ile Ala Asp Ser Gln His Arg Ser His Lys
1               5                   10                  15

Gln Met Val ( 2 ) INFORMATION FOR SEQ ID NO:31:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Zinc-binding residue"

( i x ) FEATURE:
( A ) NAME/KEY: Modified-site
( B ) LOCATION: 4
( D ) OTHER INFORMATION: /note="Zinc-binding residue"

( i x ) FEATURE:
( A ) NAME/KEY: Modified-site
( B ) LOCATION: 12
( D ) OTHER INFORMATION: /note="Zinc-binding residue"

( i x ) FEATURE:
( A ) NAME/KEY: Modified-site
( B ) LOCATION: 13
( D ) OTHER INFORMATION: /note="Replacement residue"

( i x ) FEATURE:
( A ) NAME/KEY: Modified-site
( B ) LOCATION: 15
( D ) OTHER INFORMATION: /note="Zinc-binding residue"

( i x ) FEATURE:
( A ) NAME/KEY: Modified-site
( B ) LOCATION: 16
( D ) OTHER INFORMATION: /note="Replacement residue"

( x i ) SEQUENCE DESCRIPTION: SEQ ID NO:31:

Cys Ala Thr Cys Glu Gln Ile Ala Asp Ser Gln His Lys Ser His Lys
1               5                   10                  15

Gln Met Val ( 2 ) INFORMATION FOR SEQ ID NO:32:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Zinc-binding residue"

( i x ) FEATURE:
( A ) NAME/KEY: Modified-site
( B ) LOCATION: 3
( D ) OTHER INFORMATION: /note="Replacement residue"

( i x ) FEATURE:
    ( A ) NAME/KEY: Modified-site
    ( B ) LOCATION: 4
    ( D ) OTHER INFORMATION: /note="Zinc-binding residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 15
    ( D ) OTHER INFORMATION: /note="Zinc-binding residue"

( x i ) SEQUENCE DESCRIPTION: SEQ ID NO:32:

```
Cys Ala Ser Cys Glu Gln Ile Ala Asp Ser Gln His Arg Ser His Arg
1               5                   10                  15
Gln Met Val
```

( 2 ) INFORMATION FOR SEQ ID NO:33:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 5
        ( D ) OTHER INFORMATION: /note="Replacement residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 15
        ( D ) OTHER INFORMATION: /note="Zinc-binding residue"

( x i ) SEQUENCE DESCRIPTION: SEQ ID NO:33:

```
Cys Ala Thr Cys Asp Gln Ile Ala Asp Ser Gln His Arg Ser His Arg
1               5                   10                  15
Gln Met Val
```

( 2 ) INFORMATION FOR SEQ ID NO:34:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
    ( A ) NAME/KEY: Modified-site
    ( B ) LOCATION: 4
    ( D ) OTHER INFORMATION: /note="Zinc-binding residue"

( i x ) FEATURE:
    ( A ) NAME/KEY: Modified-site
    ( B ) LOCATION: 6
    ( D ) OTHER INFORMATION: /note="Replacement residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 15
    ( D ) OTHER INFORMATION: /note="Zinc-binding residue"

( x i ) SEQUENCE DESCRIPTION: SEQ ID NO:34:

```
Cys Ala Thr Cys Glu Asn Ile Ala Asp Ser Gln His Arg Ser His Arg
1               5                   10                  15
Gln Met Val
```

( 2 ) INFORMATION FOR SEQ ID NO:35:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Zinc-binding residue"

( i x ) FEATURE:
    ( A ) NAME/KEY: Modified-site
    ( B ) LOCATION: 4
    ( D ) OTHER INFORMATION: /note="Zinc-binding residue"

( i x ) FEATURE:
    ( A ) NAME/KEY: Modified-site
    ( B ) LOCATION: 7
    ( D ) OTHER INFORMATION: /note="Replacement residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 15
    ( D ) OTHER INFORMATION: /note="Zinc-binding residue"

( x i ) SEQUENCE DESCRIPTION: SEQ ID NO:35:

```
Cys Ala Thr Cys Glu Gln Leu Ala Asp Ser Gln His Arg Ser His Arg
1               5                   10                  15
Gln Met Val
```

( 2 ) INFORMATION FOR SEQ ID NO:36:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
   ( A ) NAME/KEY: Modified-site
   ( B ) LOCATION: 1
   ( D ) OTHER INFORMATION: /note="Zinc-binding residue"

( i x ) FEATURE:
   ( A ) NAME/KEY: Modified-site
   ( B ) LOCATION: 4
   ( D ) OTHER INFORMATION: /note="Zinc-binding residue"

( i x ) FEATURE:
   ( A ) NAME/KEY: Modified-site
   ( B ) LOCATION: 7
   ( D ) OTHER INFORMATION: /note="Replacement residue"

( i x ) FEATURE:
   ( A ) NAME/KEY: Modified-site
   ( B ) LOCATION: 12
   ( D ) OTHER INFORMATION: /note="Zinc-binding residue"

( i x ) FEATURE:
   ( A ) NAME/KEY: Modified-site
   ( B ) LOCATION: 15
   ( D ) OTHER INFORMATION: /note="Zinc-binding residue"

( x i ) SEQUENCE DESCRIPTION: SEQ ID NO:36:

```
Cys Ala Thr Cys Glu Gln Val Ala Asp Ser Gln His Arg Ser His Arg
1               5                   1 0                 1 5
Gln Met Val
```

( 2 ) INFORMATION FOR SEQ ID NO:37:

( i ) SEQUENCE CHARACTERISTICS:
   ( A ) LENGTH: 19 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION: 1
   ( D ) OTHER INFORMATION: /note="Zinc-binding residue"

( i x ) FEATURE:
   ( A ) NAME/KEY: Modified-site
   ( B ) LOCATION: 4
   ( D ) OTHER INFORMATION: /note="Zinc-binding residue"

( i x ) FEATURE:
   ( A ) NAME/KEY: Modified-site
   ( B ) LOCATION: 9
   ( D ) OTHER INFORMATION: /note="Replacement residue"

( i x ) FEATURE:
   ( A ) NAME/KEY: Modified-site
   ( B ) LOCATION: 12
   ( D ) OTHER INFORMATION: /note="Zinc-binding residue"

( i x ) FEATURE:
   ( A ) NAME/KEY: Modified-site
   ( B ) LOCATION: 15
   ( D ) OTHER INFORMATION: /note="Zinc-binding residue"

( x i ) SEQUENCE DESCRIPTION: SEQ ID NO:37:

```
Cys Ala Thr Cys Glu Gln Ile Ala Glu Ser Gln His Arg Ser His Arg
1               5                   1 0                 1 5
Gln Met Val
```

( 2 ) INFORMATION FOR SEQ ID NO:38:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Zinc-binding residue"

( i x ) FEATURE:
    ( A ) NAME/KEY: Modified-site
    ( B ) LOCATION: 4
    ( D ) OTHER INFORMATION: /note="Zinc-binding residue"

( i x ) FEATURE:
    ( A ) NAME/KEY: Modified-site
    ( B ) LOCATION: 10
    ( D ) OTHER INFORMATION: /note="Replacement residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 15
    ( D ) OTHER INFORMATION: /note="Zinc-binding residue"

( x i ) SEQUENCE DESCRIPTION: SEQ ID NO:38:

```
Cys  Ala  Thr  Cys  Glu  Gln  Ile  Ala  Asp  Thr  Gln  His  Arg  Ser  His  Arg
1                  5                            10                           15

Gln  Met  Val
```

( 2 ) INFORMATION FOR SEQ ID NO:39:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Zinc-binding residue"

( i x ) FEATURE:
    ( A ) NAME/KEY: Modified-site
    ( B ) LOCATION: 4
    ( D ) OTHER INFORMATION: /note="Zinc-binding residue"

( i x ) FEATURE:
    ( A ) NAME/KEY: Modified-site
    ( B ) LOCATION: 11
    ( D ) OTHER INFORMATION: /note="Replacement residue"

( i x ) FEATURE:
    ( A ) NAME/KEY: Modified-site
    ( B ) LOCATION: 12
    ( D ) OTHER INFORMATION: /note="Zinc-binding residue"

( i x ) FEATURE:
    ( A ) NAME/KEY: Modified-site
    ( B ) LOCATION: 15
    ( D ) OTHER INFORMATION: /note="Zinc-binding residue"

( x i ) SEQUENCE DESCRIPTION: SEQ ID NO:39:

```
Cys  Ala  Thr  Cys  Glu  Gln  Ile  Ala  Asp  Ser  Asn  His  Arg  Ser  His  Arg
1                  5                            10                           15
```

Gln Met Val ( 2 ) INFORMATION FOR SEQ ID NO:40:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 14
        ( D ) OTHER INFORMATION: /note="Replacement residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 15
        ( D ) OTHER INFORMATION: /note="Zinc-binding residue"

( x i ) SEQUENCE DESCRIPTION: SEQ ID NO:40:

```
Cys Ala Thr Cys Glu Gln Ile Ala Asp Ser Gln His Arg Thr His Arg
1               5                   10                  15
Gln Met Val
```

( 2 ) INFORMATION FOR SEQ ID NO:41:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 17
        ( D ) OTHER INFORMATION: /note="Replacement residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 15

( D ) OTHER INFORMATION: /note="Zinc-binding residue"

( x i ) SEQUENCE DESCRIPTION: SEQ ID NO:41:

Cys Ala Thr Cys Glu Gln Ile Ala Asp Ser Gln His Arg Ser His Arg
1               5                   10                  15

Asn Met Val ( 2 ) INFORMATION FOR SEQ ID NO:42:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 19
        ( D ) OTHER INFORMATION: /note="Replacement residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 15
        ( D ) OTHER INFORMATION: /note="Zinc-binding residue"

( x i ) SEQUENCE DESCRIPTION: SEQ ID NO:42:

Cys Ala Thr Cys Glu Gln Ile Ala Asp Ser Gln His Arg Ser His Arg
1               5                   10                  15

Gln Met Leu ( 2 ) INFORMATION FOR SEQ ID NO:43:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site (B) LOCATION: 15
(D) OTHER INFORMATION: /note="Zinc-binding residue"

(ix) FEATURE:
(A) NAME/KEY: Modified-site
(B) LOCATION: 19
(D) OTHER INFORMATION: /note="Replacement residue"

(xi) SEQUENCE DESCRIPTION: SEQ ID NO:43:

Cys Ala Thr Cys Glu Gln Ile Ala Asp Ser Gln His Arg Ser His Arg
1               5                   10                  15

Gln Met Ile (2) INFORMATION FOR SEQ ID NO:44:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Zinc-binding residue"

(ix) FEATURE:
(A) NAME/KEY: Modified-site
(B) LOCATION: 4
(D) OTHER INFORMATION: /note="Zinc-binding residue"

(ix) FEATURE:
(A) NAME/KEY: Modified-site
(B) LOCATION: 12
(D) OTHER INFORMATION: /note="Zinc-binding residue"

(ix) FEATURE:
(A) NAME/KEY: Modified-site
(B) LOCATION: 15
(D) OTHER INFORMATION: /note="Zinc-binding residue"

(ix) FEATURE:
(A) NAME/KEY: Modified-site
(B) LOCATION: 2
(D) OTHER INFORMATION: /note="This is a replacement
residue and it is D-Ala"

(xi) SEQUENCE DESCRIPTION: SEQ ID NO:44:

Cys Xaa Thr Cys Glu Gln Ile Ala Asp Ser Gln His Arg Ser His Arg
1               5                   10                  15

Gln Met Val (2) INFORMATION FOR SEQ ID NO:45:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Zinc-binding residue"

(ix) FEATURE:
(A) NAME/KEY: Modified-site
(B) LOCATION: 4
(D) OTHER INFORMATION: /note="Zinc-binding residue"

( i x ) FEATURE:
  ( A ) NAME/KEY: Modified-site
  ( B ) LOCATION: 12
  ( D ) OTHER INFORMATION: /note="Zinc-binding residue"

( i x ) FEATURE:
  ( A ) NAME/KEY: Modified-site
  ( B ) LOCATION: 15
  ( D ) OTHER INFORMATION: /note="Zinc-binding residue"

( i x ) FEATURE:
  ( A ) NAME/KEY: Modified-site
  ( B ) LOCATION: 13
  ( D ) OTHER INFORMATION: /note="This position is D-Arg and it is a replacement residue"

( x i ) SEQUENCE DESCRIPTION: SEQ ID NO:45:

Cys Ala Thr Cys Glu Gln Ile Ala Asp Ser Gln His Xaa Ser His Arg
1       5          10         15

Gln Met Val ( 2 ) INFORMATION FOR SEQ ID NO:46:

( i ) SEQUENCE CHARACTERISTICS:
  ( A ) LENGTH: 19 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note="Zinc-binding residue"

( i x ) FEATURE:
  ( A ) NAME/KEY: Modified-site
  ( B ) LOCATION: 4
  ( D ) OTHER INFORMATION: /note="Zinc-binding residue"

( i x ) FEATURE:
  ( A ) NAME/KEY: Modified-site
  ( B ) LOCATION: 12
  ( D ) OTHER INFORMATION: /note="Zinc-binding residue"

( i x ) FEATURE:
  ( A ) NAME/KEY: Modified-site
  ( B ) LOCATION: 15
  ( D ) OTHER INFORMATION: /note="Zinc-binding residue"

( i x ) FEATURE:
  ( A ) NAME/KEY: Modified-site
  ( B ) LOCATION: 16
  ( D ) OTHER INFORMATION: /note="This position is D-Arg and it is a replacement residue"

( x i ) SEQUENCE DESCRIPTION: SEQ ID NO:46:

Cys Ala Thr Cys Glu Gln Ile Ala Asp Ser Gln His Arg Ser His Xaa
1       5          10         15

Gln Met Val ( 2 ) INFORMATION FOR SEQ ID NO:47:

( i ) SEQUENCE CHARACTERISTICS:
  ( A ) LENGTH: 19 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site (B) LOCATION: 1
(D) OTHER INFORMATION: /note="Zinc-binding residue"

(ix) FEATURE:
(A) NAME/KEY: Modified-site
(B) LOCATION: 4
(D) OTHER INFORMATION: /note="Zinc-binding residue"

(ix) FEATURE:
(A) NAME/KEY: Modified-site
(B) LOCATION: 12
(D) OTHER INFORMATION: /note="Zinc-binding residue"

(ix) FEATURE:
(A) NAME/KEY: Modified-site
(B) LOCATION: 15
(D) OTHER INFORMATION: /note="Zinc-binding residue"

(ix) FEATURE:
(A) NAME/KEY: Modified-site
(B) LOCATION: 2
(D) OTHER INFORMATION: /note="This is a replacement residue and it is D-Ala"

(ix) FEATURE:
(A) NAME/KEY: Modified-site
(B) LOCATION: 13
(D) OTHER INFORMATION: /note="This is a replacement residue and it is D-Arg"

(xi) SEQUENCE DESCRIPTION: SEQ ID NO:47:

Cys Xaa Thr Cys Glu Gln Ile Ala Asp Ser Gln His Xaa Ser His Arg
1               5                   10                  15
Gln Met Val (2) INFORMATION FOR SEQ ID NO:48:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Zinc-binding residue"

(ix) FEATURE:
(A) NAME/KEY: Modified-site
(B) LOCATION: 4
(D) OTHER INFORMATION: /note="Zinc-binding residue"

(ix) FEATURE:
(A) NAME/KEY: Modified-site
(B) LOCATION: 12
(D) OTHER INFORMATION: /note="Zinc-binding residue"

(ix) FEATURE:
(A) NAME/KEY: Modified-site
(B) LOCATION: 15
(D) OTHER INFORMATION: /note="Zinc-binding residue"

(ix) FEATURE:
(A) NAME/KEY: Modified-site
(B) LOCATION: 2
(D) OTHER INFORMATION: /note="This is a replacement residue and it is D-Ala"

(ix) FEATURE:
(A) NAME/KEY: Modified-site
(B) LOCATION: 13
(D) OTHER INFORMATION: /note="This is a replacement residue and it is D-Arg"

( i x ) FEATURE:
    ( A ) NAME/KEY: Modified-site
    ( B ) LOCATION: 16
    ( D ) OTHER INFORMATION: /note="This is a replacement
        residue and it is D-Arg"

( x i ) SEQUENCE DESCRIPTION: SEQ ID NO:48:

Cys Xaa Thr Cys Glu Gln Ile Ala Asp Ser Gln His Xaa Ser His Xaa
1               5                   10                  15

Gln Met Val ( 2 ) INFORMATION FOR SEQ ID NO:49:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site
        ( B ) LOCATION: 12
        ( D ) OTHER INFORMATION: /note="Zinc-binding residue"

( i x ) FEATURE:
        ( A ) NAME/KEY: Modified-site
        ( B ) LOCATION: 15
        ( D ) OTHER INFORMATION: /note="Zinc-binding residue"

( i x ) FEATURE:
        ( A ) NAME/KEY: Modified-site
        ( B ) LOCATION: 2
        ( D ) OTHER INFORMATION: /note="This is a replacement
        residue and it is NMe-Ala"

( x i ) SEQUENCE DESCRIPTION: SEQ ID NO:49:

Cys Xaa Thr Cys Glu Gln Ile Ala Asp Ser Gln His Arg Ser His Arg
1               5                   10                  15

Gln Met Val ( 2 ) INFORMATION FOR SEQ ID NO:50:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Zinc-binding residue"

( i x ) FEATURE:
        ( A ) NAME/KEY: Modified-site
        ( B ) LOCATION: 4
        ( D ) OTHER INFORMATION: /note="Zinc-binding residue"

( i x ) FEATURE:
        ( A ) NAME/KEY: Modified-site (B) LOCATION: 12
(D) OTHER INFORMATION: /note="Zinc-binding residue"

(ix) FEATURE:
(A) NAME/KEY: Modified-site
(B) LOCATION: 15
(D) OTHER INFORMATION: /note="Zinc-binding residue"

(ix) FEATURE:
(A) NAME/KEY: Modified-site
(B) LOCATION: 13
(D) OTHER INFORMATION: /note="This position is N-MeArg"

(xi) SEQUENCE DESCRIPTION: SEQ ID NO:50:

```
Cys Ala Thr Cys Glu Gln Ile Ala Asp Ser Gln His Xaa Ser His Arg
1               5                   10                  15

Gln Met Val
```

(2) INFORMATION FOR SEQ ID NO:51:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Zinc-binding residue"

(ix) FEATURE:
(A) NAME/KEY: Modified-site
(B) LOCATION: 4
(D) OTHER INFORMATION: /note="Zinc-binding residue"

(ix) FEATURE:
(A) NAME/KEY: Modified-site
(B) LOCATION: 12
(D) OTHER INFORMATION: /note="Zinc-binding residue"

(ix) FEATURE:
(A) NAME/KEY: Modified-site
(B) LOCATION: 15
(D) OTHER INFORMATION: /note="Zinc-binding residue"

(ix) FEATURE:
(A) NAME/KEY: Modified-site
(B) LOCATION: 16
(D) OTHER INFORMATION: /note="This position is N-MeArg"

(xi) SEQUENCE DESCRIPTION: SEQ ID NO:51:

```
Cys Ala Thr Cys Glu Gln Ile Ala Asp Ser Gln His Arg Ser His Xaa
1               5                   10                  15

Gln Met Val
```

(2) INFORMATION FOR SEQ ID NO:52:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Zinc-binding residue"

( i x ) FEATURE:
  ( A ) NAME/KEY: Modified-site
  ( B ) LOCATION: 4
  ( D ) OTHER INFORMATION: /note="Zinc-binding residue"

( i x ) FEATURE:
  ( A ) NAME/KEY: Modified-site
  ( B ) LOCATION: 12
  ( D ) OTHER INFORMATION: /note="Zinc-binding residue"

( i x ) FEATURE:
  ( A ) NAME/KEY: Modified-site
  ( B ) LOCATION: 15
  ( D ) OTHER INFORMATION: /note="Zinc-binding residue"

( i x ) FEATURE:
  ( A ) NAME/KEY: Modified-site
  ( B ) LOCATION: 2
  ( D ) OTHER INFORMATION: /note="This is a replacement
    residue and it is NMe-Ala"

( i x ) FEATURE:
  ( A ) NAME/KEY: Modified-site
  ( B ) LOCATION: 13
  ( D ) OTHER INFORMATION: /note="This is a replacement
    residue and it is NMe-Arg"

( x i ) SEQUENCE DESCRIPTION: SEQ ID NO:52:

Cys Xaa Thr Cys Glu Gln Ile Ala Asp Ser Gln His Xaa Ser His Arg
1      5        10        15

Gln Met Val ( 2 ) INFORMATION FOR SEQ ID NO:53:

( i ) SEQUENCE CHARACTERISTICS:
  ( A ) LENGTH: 19 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note="Zinc-binding residue"

( i x ) FEATURE:
  ( A ) NAME/KEY: Modified-site
  ( B ) LOCATION: 4
  ( D ) OTHER INFORMATION: /note="Zinc-binding residue"

( i x ) FEATURE:
  ( A ) NAME/KEY: Modified-site
  ( B ) LOCATION: 12
  ( D ) OTHER INFORMATION: /note="Zinc-binding residue"

( i x ) FEATURE:
  ( A ) NAME/KEY: Modified-site
  ( B ) LOCATION: 15
  ( D ) OTHER INFORMATION: /note="Zinc-binding residue"

( i x ) FEATURE:
  ( A ) NAME/KEY: Modified-site
  ( B ) LOCATION: 2
  ( D ) OTHER INFORMATION: /note="This is a replacement
    residue and it is NMe-Ala"

( i x ) FEATURE:
  ( A ) NAME/KEY: Modified-site
  ( B ) LOCATION: 13
  ( D ) OTHER INFORMATION: /note="This is a replacement
    residue and it is NMe-Arg"

( i x ) FEATURE:
  ( A ) NAME/KEY: Modified-site ( B ) LOCATION: 16
( D ) OTHER INFORMATION: /note="This is a replacement residue and it is NMe-Arg"

( x i ) SEQUENCE DESCRIPTION: SEQ ID NO:53:

Cys Xaa Thr Cys Glu Gln Ile Ala Asp Ser Gln His Xaa Ser His Xaa
1               5                   10                  15

Gln Met Val ( 2 ) INFORMATION FOR SEQ ID NO:54:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:54:

Leu Thr Val Pro Ser Glu Arg Gly Leu Gln Arg Arg Arg
1               5                   10

( 2 ) INFORMATION FOR SEQ ID NO:55:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:55:

Ala Leu Asn Gly Asn Gly Asp Pro Asn Asn Met Asp Lys Ala Val Lys
1               5                   10                  15

Leu Tyr ( 2 ) INFORMATION FOR SEQ ID NO:56:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:56:

Lys Arg Glu Ile Thr Phe His Gly Ala Lys Glu Ile Ser Leu Ser
1               5                   10                  15

( 2 ) INFORMATION FOR SEQ ID NO:57:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:57:

Glu Gln Ile Ala Asp Ser Gln His Arg Ser His Arg Gln Met Val
1               5                   10                  15

( 2 ) INFORMATION FOR SEQ ID NO:58:

(i) SEQUENCE CHARACTERISTICS:
    (A) LENGTH: 17 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:58:

Gly Thr His Pro Ser Ser Ser Ala Gly Leu Lys Asn Asp Leu Leu Glu
1               5                   10                  15
Asn (2) INFORMATION FOR SEQ ID NO:59:

(i) SEQUENCE CHARACTERISTICS:
    (A) LENGTH: 19 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:59:

Cys Ala Thr Cys Glu Gln Ile Ala Asp Ser Gln His Arg Ser His Arg
1               5                   10                  15
Gln Met Val

M-PROTEIN PEPTIDES OF INFLUENZA VIRUS AS ANTIVIRAL AGENTS

Reference to Related Application

This application is a continuation of U.S. patent application Ser. No. 07/821,031, filed Jan. 16, 1992, abandoned, which is a continuation-in-part of U.S. patent application Ser. No. 717,429, filed 19 Jun. 1991, now abandoned.

BACKGROUND OF THE INVENTION

1. Field of the Invention

This invention relates to peptide-based antiviral agents and their use. More particularly it concerns peptide-based antiviral agents substantially corresponding in sequence to a region of influenza matrix protein.

2. Description of Prior Work

Influenza viruses, a class of single-stranded RNA virus, continue to cause serious respiratory disease throughout the world. Type A influenza virus causes pneumonia and deaths, especially in the elderly. Type B influenza viruses tend to infect a younger age population than does type A and are associated with Reye's syndrome. With antigenic drift, type B influenza viruses are capable of producing disease in all ages of the population. The economic costs of influenza are considerable: the annual costs of disease due to influenza in the U.S. are estimated to be between 4.6 billion dollars and 10 billion dollars.

Influenza is not a trivial disease. Although a typical influenza case may be limited to fever, sore throat, and several days of malaise with subsequent uneventful recovery, more severe lung disease, primary viral pneumonia, or secondary bacterial pneumonia can occur (Advisory Committee on Immunization Practices, MMWR 35, 317–331 (1986)). The elderly or those who suffer from cardiopulmonary or other chronic lung diseases are at special risk.

The only effective antiviral drugs for influenza are amantadine or its close relative rimantadine. Although these drugs can be quite effective against influenza, they are effective only against disease caused by type A influenza virus and are not well tolerated in the group of individuals at highest risk of morbidity and mortality—the elderly. In individuals with poor renal clearance, the drugs may accumulate, producing convulsion; other CNS effects are light-headedness, dizziness, and problems in concentrating (id.; and Dolin and Bentley in "Options for the Control of Influenza," Kenda and Patriarca (eds.), Alan R. Liss, Inc., New York 1986, pp. 317–326). In addition, the drug works most effectively as a prophylactic agent; therefore, one risks side effects in the absence of actual infection with influenza. Considerable morbidity and mortality also occur with type B influenza, which was responsible for the major epidemic illness in four out of the last ten influenza epidemics in the United States (MMWR 35, 470–479 (1986)).

The present invention provides an antiviral agent that functions by targeting the viral transcription. These agents are not only specific for influenza virus, but are also free of the antigenic shift and drift associated with the surface antigens of influenza virus, i.e., hemagglutinin and neuraminidase. Thus these antiviral agents have a broad spectrum, inhibiting the transcription of type A as well as type B influenza viruses, with possible extension to the RNA polymerases of other negative-strand viruses, including the paramyxovirus and rhabdovirus groups responsible for human and veterinary disease.

$M_1$ ("matrix protein") is a major structural component of the influenza virion, constituting approximately 30% of the total viral protein and occupying the key location between the surface glycoprotein of the envelope and the ribonucleoprotein complex (Virology 42, 890–904 (1979)). $M_1$ incorporates into lipid bilayers either as liposomes or planar bilayer lipid membranes (Bucher, D. J. et al., J. Virol. 36, 586–590 (1980); Bucher, D. J. et al., Intervirology 14, 69–77 (1988); and Kahn, M. W. et al., J. Clin. Microbiol. 16, 115–122 (1982)).

$M_1$ has been shown to inhibit influenza virus transcription, and this activity has been shown to be localized in the 15 kd amino terminal fragment (Zavonarjev and Ghendon, J. Virol. 33, 583–586 (1980); and Ye, Z. et al., J. Virol. 61, 239–246 (1987)). This effect can be reversed by monoclonal antibodies (Hankins, R. W. et al., Virus Genes 3, 111–126 (1989)). Ye, Z. et al., J. Virol. 63, 3586–3594 (1989), studied the transcription inhibition and determined the RNA binding domains using anti-idiotypic antibodies and synthetic peptides. As background, we performed immunofluorescence analysis of $M_1$ with monoclonal antibodies (MAbs) and observed the migration of $M_1$ to the nucleus during the replicative cycle and the association of $M_1$ with actin filaments in the cytoplasm (Bucher, D. et al., J. Virol. 63, 3622–3633 (1989)). $M_1$ is highly conserved, unlike the highly mutable surface antigens hemagglutinin and neuraminidase. Comparison of the amino acid sequence of $M_1$ from influenza strain A/PR/8/34 and strain A/Udorn/72 shows only seven amino acids changed over a period of 38 years (Winter and Fields, Nucleic Acids Res. 8, 1965–1974 (1980; and Lamb and Lai, Virology 112, 746–751 (1981)). Furthermore, these changes are conservative, including such alterations as Ile→Ala, and Arg→Lys. Antigenic drift in hemagglutinin occurs at a rate of 0.9–1% of the amino acids/year within a subtype, as seen for A/NT/60/68 versus A/Bangkok/79 strains (Huddleston and Brownlee, Nucleic Acids Res. 10, 1029–1038 (1982)). Overall sequence homology between $M_1$ of type A and type B is found to be 54%; however, in certain regions there is more than 70% homology. Thus, it is likely that a peptide antiviral with a broad spectrum of activity (both A and B types) will result if it incorporates conserved sequences present in $M_1$ with virus transcription inhibitory activity.

Other related work with $M_1$ protein has demonstrated that $M_1$ will incorporate into lipid bilayers liposomes or planar membranes (Bucher 1980, supra). Antibody response to the $M_1$ component in a clinical population that was immunized with influenza vaccine or infected with wild-type circulating virus has been studied (Khan, M. W. et al., J. Clin. Microbiol. 16, 813 (1982)). It has been demonstrated that $M_1$ can be an effective target for universal detection of type A influenza viruses in clinical specimens (Bucher, D. J. et al., J. Immunol. Methods 96, 77–85 (1987)). A panel of monoclonal antibodies to several antigenic sites of $M_1$ has been developed and used in virus detection (id.; and Bucher, D. et al., VIIth International Congress of Virology, Edmonton, Canada, Abstract, R2328). We have localized three immunoreactive segments of $M_1$ using synthetic peptides (Bucher 1989, supra; and U.S. Pat. No. 4,981,782).

While these earlier studies have provided valuable insight into the mechanism and potential prevention of influenza infection through immunization, an important need remains for agents which will intervene in the disease by direct antiviral action. It is this need that the present invention addresses.

References

The following references were collected by the inventors and relate to the general subject of influenza, influenza virus, antiviral activity of peptides and the like. Many of the references are cited throughout this document.

1. National Academy of Sciences. New vaccine development. Establishing priorities. Vol. I. Diseases of Importance in the United States, Washington, D.C., National Academy Press, Appendix K, Prospects for immunizing against influenza viruses A and B (1985).
2. Advisory Committee on Immunization Practices (ACIP). Prevention and control of influenza. MMWR 35, 317–331 (1986).
3. R. Dolin and D. W. Bentley. Amantadine and rimantadine: prophylaxis and therapy of influenza A in adults. In "Options for the Control of Influenza. A. P. Kenda and P. A. Patriarca (eds.). Alan R. Liss, Inc., New York 1986, pp. 317–326.
4. Centers for Disease Control (CDC). Influenza-United States, 1985–1986 season. *MMWR* 35, 470–479 (1986).
5. I. T. Schulze. The structure of influenza virus. I. The polypeptide of the virion. *Virology* 42, 890–904 (1979).
6. D. J. Bucher, I. G. Kharitonenkov, J. A. Zakomirdin, V. B. Gregoriev, S. M. Klimenko, and J. F. Davis. Incorporation of influenza virus M-protein into liposomes. *J. Virol.* 36, 586–590 (1980).
7. D. J. Bucher, I. G. Kharitonenkov, D. K. Lvov, T. V. Pysine, and H. M. Lee. Comparative study of influenza virus $H_2$ (Asian) heamgglutinins isolated from human and avian sources. *Intervirology* 14 69–77 (1988).
8. M. W. Khan, M. Gallagher, D. Bucher, C. P. Cerini, and E. D. Kilbourne. Detection of influenza virus neuraminidase-specific antibodies by an enzyme-linked immunosorbent assay. *J. Clin. Microbiol.* 16, 115–122 (1982).
9. A. Y. Zavonarjev and Y. Z. Ghendon. Influence of membrane (M) protein on influenza A virus virion transcript activity in vitro and its susceptibility to rimantadine. *J. Virol.* 33, 583–586 (1980).
10. Z. Ye, R. Pal, J. W. Fox, and R. R. Wagner. Functional and antigenic domains of the matrix (M) protein of influenza A virus. *J. Virol.* 61, 239–246 (1987).
11. R. W. Hankins, K. Nagata, D. J. Bucher, S. Popple, and A. Ishihama. Monoclonal antibody analysis of influenza virus matrix protein epitopes involved in transcription inhibition. *Virus Genes* 3, 111–126 (1989).
12. Z. Ye, N. W. Baylor, and R. R. Wagner. Transcription-inhibition and RNA-binding domains of influenza A virus matrix protein mapped with anti-idiotypic antibodies and synthetic peptides. *J. Virol.* 63, 3586–3594 (1989).
13. D. Bucher, S. Popple, M. Baer, A. Mikhail, Y. -F. Gong, C. Whiteker, E. Paoletti, and A. Judd. M protein (M1) of influenza virus: Antigenic analysis and intracellular localization with monoclonal antibodies. *J. Virol.* 63, 3622–3633 (1989).
14. G. Winter and S. Fields. Cloning of influenza DNA into M1. The sequence of the RNA segment encoding the A/PR/8/34 matrix protein. *Nucleic Acids Res.* 8, 1965–1974 (1980).
15. R. A. Lamb and C. J. Lai. Conservation of the influenza virus membrane protein (M1) amino acid sequence and an open reading frame of RNA segment 7 encoding a second protein (M2) in H1N1 and H3N3 strains. *Virology* 112,746–751 (1981).
16. J. A. Huddleston and G. G. Brownlee. The sequence of the nucleoprotein gene of human influenza A virus strain A/NT/60/68. *Nucleic Acids Res.* 10, 1029–1038 (1982).
17. D. J. Bucher. Chromatographic isolation of the major polypeptides of influenza virus. In The Negative Strand Viruses. B. W. J. Mahy and R. D. Barry (eds.), Vol. I, Academic Press, 1975, pp. 133–143.
18. D. J. Bucher, S. S. -L. Li, J. M. Kehoe, and E. D. Kilbourne. Chromatographic isolation of the hemagglutinin polypeptides from influenza virus vaccine and determination of their amino terminal sequences. *Proc. Natl. Acad. Sci. USA* 73, 238–242 (1976).
19. D. J. Bucher. Purification of neuraminidase from influenza viruses by affinity chromatography. *Biochim. Biophys. Acta* 483, 393–399 (1977).
20. M. Gallagher, D. J. Bucher, R. Dourmashkin, J. F. Davis, G. Rosenn, and E. D. Kilbourne. Isolation of immunogenic neuraminidases of human influenza viruses by a combination of genetic and biochemical procedures. *J. Clin. Microbiol.* 20, 89–93 (1984).
21. M. W. Khan, D. J. Bucher, A. K. Koul, G. Kalish, and E. D. Kilbourne. Detection of antibodies to influenza virus M protein by an enzyme-linked immunosorbent assay. *J. Clin. Microbiol.* 16, 813 (1982).
22. D. J. Bucher, I. G. Kharitonenkov, M. W. Khan, A. Palo, D. Holloway, and A. Mikhail. Detection of influenza viruses through selective adsorption and detection of the M-protein antigen. *J. Immunol. Methods* 96, 77–85 (1987).
23. D. Bucher, A. Mikhail. S. Popple, M. Baer, and C. Whitaker. Rapid detection of influenza viruses with monoclonal antibodies to M-protein. VIIth International Congress of Virology, Edmonton, Canada, Abstract, R2328.
24. A. K. Judd, D. J. Bucher, and S. W. Popple. Synthetic peptides for diagnosis and prevention of influenza virus infection and their use. U.S. Pat. No. 4,981,782, Jan. 1, 1991.
25. B. W. Erickson and R. B. Merrifield. Solid phase peptide synthesis. In The Proteins, vol. II. H. Neurath (ed.), Academic Press, Inc., New York, pp. 255–527 (1976).
26. D. J. Bucher, I. G. Kharitonenkov, J. A. Zakomirdin, V. B. Gregoriev, S. M. Klimenko, and J. F. Davis. Incorporation of influenza virus M-protein into liposomes. *J. Virol.* 36, 586–590 (1980).
27. O. M. Rochovansky. RNA synthesis by ribonucleoprotein-polymerase complexes isolated from influenza virus. *Virology* 73, 327–338 (1976).
28. J. J. Plotch, M. Bouloy, I. Ulmann, and R. M. Krug. A unique cap ($M^7$GippXm) dependent influenza virion endonuclease cleaves capped RNAs to generate the primers that initiate viral transcription. *Cell* 23, 847–858 (1981).
29. A. Kato, K. Mizumoto, and A. Ishihama. Purification and enzymatic properties of an RNA polymerase -RNA complex from influenza virus. *Virus Res.* 3, 115–127 (1985).
30. R. G. Almquist, W. -R. Chao, A. K. Judd, C. Mitoma, D. J. Rossi, R. E. Panasevich, and R. J. Matthews. Synthesis and biological activity of ketomethylene-containing monopeptide analogs of snake venom angiotensin converting enzyme inhibitors. *J. Med. Chem.* 31, 561 (1988).

31. J. M. Stewart and J. D. Young. In Solid Phase Peptide Synthesis. J. M. Stewart and J. D. Young (eds.). Pierce Chemical Co., 1984, p. 83.

32. S. L. Harbeson and D. H. Rich. Inhibition of aminopeptidases by peptides containing ketomethylene and hydroxyethylene amide bond replacements. *J. Med. Chem.* 32, 1378–1392 (1989).

33. M. T. Garcia-Lopez, R. Gonzalez-Muniz, and J. R. Harto. Synthesis of ketomethylene dipeptides containing basic amino acid analogs of C-terminus. *Tetrahedron* 44, 5131–5138 (1988).

34. M. T. Garcia-Lopez, R. Gonzalez-Muniz, and J. R. Harto. A simple and versatile route to ketomethylene dipeptide analogs. *Tetrahedron Lett.* 29, 1577–1580 (1988).

35. R. L. Johnson and R. B. Miller. Use of triphenylmethyl (trityl) amino protecting group in the synthesis of ketomethylene analogs of peptides. *Int. J. Peptide Protein Res.* 23, 581–590 (1984).

36. J. V. N. V. Prasad and D. H. Rich. Addition of allylic metals for α-amino aldehydes. Application to the synthesis of statin, ketomethylene and hydroethylene dipeptide diesters. *Tetrahedron Lett.* 31, 1803–1806 (1990).

37. B. E. Evans, K. E. Rittle, C. F. Homnick, J. P. Springer, J. Hirshfield, and D. F. Veber. A stereocontrolled synthesis of hydroxyethylene dipeptide isosteres using novel, chiral aminoalkyl epoxides and γ-(aminoalkyl) γ-lactones. *J. Org. Chem.* 50, 4615–4625 (1985).

38. A. H. Fray, R. L. Kaye, and E. F. Kleinman. A short stereoselective synthesis of the lactone precursor to 2R,4S,5S hydroxyethylene dipeptide isosteres. *J. Org. Chem.* 51, 4828–4833 (1986).

39. K. Deres, H. Schild, K. -H., Wiesmüller, G. Jung, and H. -G. Rammensee. In vivo priming of virus-specific cytotoxic T lymphocytes with synthetic lipopeptide vaccine. *Nature* 342, 561–564 (1989).

40. I. Toth, R. A. Hughes, M. R. Munday, P. Mascagni, and W. A. Gibbons. A novel oligopeptide delivery system for poorly adsorbed peptides and drugs. In Proceedings of the Eleventh American Peptide Symposium. J. E. Rivier and G. R. Marshall (eds.), ESCOM, Leiden, pp. 1078–1079 (1990).

41. Y. Sanchez, I. Ionescu-Matiu, G. R. Dreesman, W. Kramp, H. R. Six, F. B. Hollinger, and J. L. Melnick. Humoral and cellular immunity to hepatitis B virus-derived antigens: comparative activity of Freund's complete adjuvant, alum, and liposomes. *Infect. Immun.* 30, 728–733 (1980).

42. G. W. Both and G. M. Air. Nucleotide sequence coding for the N-terminal region of the matrix protein of influenza virus. *Eur. J. Biochem.* 96, 363–372 (1970).

43. B. E. Johansson, D. J. Bucher, and E. D. Kilbourne. Purified influenza virus hemagglutinin and neuraminidase are equivalent in stimulation of antibody response but induce contrasting types of immunity to infection. *J. Virol.* 63, 1239–1246 (1989).

44. A. Gregorriades. Influenza virus-induced proteins in nuclei and cytoplasm of infected cells. *Virology* 79, 449–454 (1977).

STATEMENT OF THE INVENTION

We have now found that synthetic peptides substantially corresponding to the 148–166 region of influenza A matrix protein ($M_1$) exhibit activity as influenza transcription inhibitors that is significantly higher than that shown by the matrix protein itself. These peptides thus serve as active antiviral agents. In one aspect this invention provides these active peptides themselves and their analogs. In another aspect this invention provides antiviral compositions which include these peptides and antiviral therapies employing these compositions.

BRIEF DESCRIPTION OF THE DRAWINGS

This invention will be described with reference being made to the accompanying drawings in which.

DETAILED DESCRIPTION OF THE INVENTION

Nomenclature and Definitions

Figure 1:
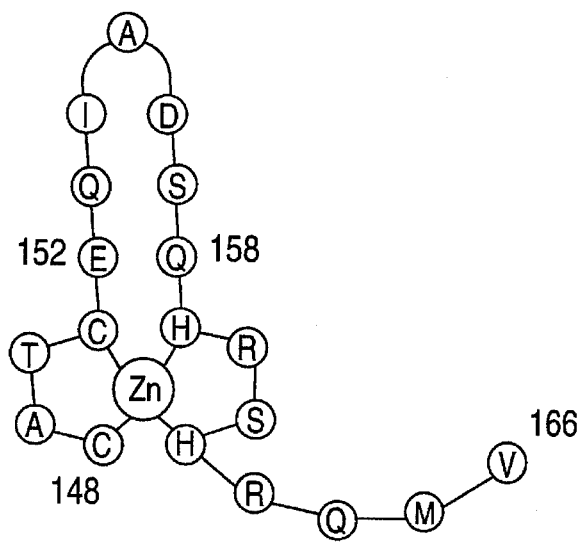
FIG. 1 (SEQ ID NO: 59) is a schematic illustration of a peptide of this invention illustrating a proposed mechanism for its inhibitory activity.

In this description and claims reference shall be made to the common L amino acids and achiral glycine using the following single-letter symbols:

| Amino Acid | One-Letter Symbol |
| --- | --- |
| Alanine | A |
| Arginine | R |
| Asparagine | N |
| Aspartic acid | D |
| Asparagine or aspartic acid | B |
| Cysteine | C |
| Glutamine | Q |
| Glutamic acid | E |
| Glutamine or glutamic acid | Z |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

The less common amino acids are referenced by three-letter codes: D-Ala for D-alanine, NMe-Ala for N-methylalanine, D-Arg for D-arginine, and NMe-Arg for N-methylarginine. These peptides are depicted in sequence with their amino ends to the left and acid ends to the right.

"Acyl" refers to an alkyl-containing carbonyl group, e.g., R—C(=O)—, wherein R is an alkyl group having from 1 to 8 carbon atoms, such as methyl, ethyl, n-propyl, isopropyl, hexyl, octyl and the like. The acyl group usually preferred in this invention is acetyl. Acyl groups are used to block the terminal amino group of a polypeptide.

"Influenza" refers to a disease state brought about by infection by an influenza virus. Among the influenza viruses are type A and type B viruses. These type A and B are recognized in the field. A number of these have been identified and are present in and available from the American Type Culture Collection. These representative materials are described at pages 272–276 in "American Type Culture Collection Catalogue of Strains II, Fourth Edition" (1983), R. Hay et al., eds., American Type Culture Collection, Rockville, Md., which is incorporated herein by reference.

"Conjugate" refers to an antigen or hapten chemically bonded to a carrier; a conjugate can contain other groups, as well.

"Corresponding" or "substantially corresponding" refers to the property of two amino acid sequences being identical to one another or differing from one another by no more than about 4 or 5 amino acid units. Sequences can differ by having a different amino acid at a given position or by having an extra amino acid or by missing an amino acid. Preferably, the sequences have at most 1 to 4 points of difference. A further defining description of this term in this setting is given below.

"Lower alkyl" refers to a straight- or branched-chain saturated hydrocarbon group having from 1 to 4 carbon atoms such as, for example, methyl, ethyl, n-propyl, isopropyl, n-butyl, isobutyl, sec-butyl, and tert-butyl.

"Matrix protein" or "M protein" or "$M_1$" refers to a protein constituent of influenza and related viruses. It is described in detail herein in the Background section.

"Peptide" or "polypeptide" refers to relatively low molecular weight compounds which yield two or more amino acids upon hydrolysis.

"Pharmaceutically acceptable salt" and "salt" refer to salts that retain the desired antiviral activity of the parent polypeptide. "Pharmaceutically acceptable salt" refers to salts that are suitable for ingestion or parenteral administration or the like in that they do not impart any undesired toxicological effects. Examples of such salts and pharmaceutically acceptable salts include (a) acid addition salts formed with inorganic acids, for example hydrochloric acid, hydrobromic acid, sulfuric acid, phosphoric acid,nitric acid and the like; and salts formed with organic acid such as, for example, acetic acid, oxalic acid, tartaric acid, succinic acid, maleic acid, fumaric acid, gluconic acid, citric acid, malic acid, ascorbic acid, benzoic acid, tannic acid, alginic acid, polyglutamic acid, naphthalenesulfonic acids, naphthalenedisulfonic acids, polygalacturonic acid, and the like; (b) salt with monovalent and polyvalent metal cations such as sodium, potassium, zinc, calcium, barium, magnesium, aluminum, copper, cobalt, nickel, cadmium, and the like; or with an organic cation formed from N,N'-dibenzylethylenediamine or ethylenediamine; and (c) combinations of (a) and (b), e.g., a zinc tannate salt and the like.

"Conservative substitution" is used to refer to an amino acid substitution in a peptide which does not interfere with or decrease the antiviral or inhibitory activity of the peptide.

The Peptides

The peptides of this invention correspond substantially to the 148–166 region of influenza A matrix protein. This region in the native material has the sequence:

| 148 | 166 |
|---|---|
| C—A—T—C—E—Q—I—A—D—S—Q—H—R—S—H—R—Q—M—V (SEQ ID NO: 1) | |

A peptide is defined to "correspond substantially" to this region if it has the following features:

It has first and second C residues corresponding to the native 148 and 151 C residues spaced apart by one or two amino acid residues and first and second H residues corresponding to the native 159 and 162 H residues spaced apart by one or two amino acid residues with from 4 to 7 residues spacing between the second C and first H residues, and it includes at least about 1 and up to 7 amino acid residues beyond the second H residue, and It has a total of 12 to 20 amino acids, at least 75% of which are the amino acids of the native material in the same sequence (allowing for deletions and additions) present in the native material.

Using these criteria, the amino acids can be defined as follows:

AAa1-AAa2-AAa3-C1-AAb1-AAb2-C2-AAc1-AAc2-AAc3-AAc4-AAc5-AAc6-AAc7-H1-AAd1-AAd2-H2-AAe1-AAe2-AAe3-AAe4-AAe5-AAe6

In the formula:

AAa1 is deleted or G or a conservative substitution for G, such as A or L;

AAa2 is deleted or L or a conservative substitution for L, such as I or V;

AAa3 is deleted or V or a conservative substitution for V, such as I, L, or A.

Preferably all of AAal, 2, 3 are deleted in which case optionally the $NH_2$ group then free on C may be acylated.

AAb1 is deleted or A or a conservative substitution for A, such as D-ala or NMe-ala;

AAb2 is deleted or T or a conservative substitution for T, such as S.

Preferably at least one and more preferably both of AAb1 and AAb2 are present and exist in their native forms of A and T, respectively.

AAc1 is E, or deleted or a conservative substitution for E, such as D;

AAc2 is Q, or deleted or a conservative substitution for Q, such as N;

AAc3 is I, or deleted or a conservative substitution for I, such as L or V;

AAc4 is A, or deleted or a conservative substitution for A, such as L;

AAc5 is D, or deleted or a conservative substitution for D, such as E;

AAc6 is S, or deleted or a conservative substitution for S, such as A or T;

AAc7 is Q, or deleted or a conservative substitution for Q, such as A or N.

Preferably from 0 to 4 of these AAc adjacent amino acids are omitted or at most 1 or 2 amino acids in this AAc sequence are substituted:

AAd1 is R, or deleted or a conservative substitution for R, such as A or K;

AAd2 is S, or deleted or a conservative substitution for S, such as A or T.

Preferably at least one of AAd1 and AAd2 is present in its native form. More preferably both are present in their native forms.

AAe1 is R or deleted or a conservative substitution for R such as D-arg or K;

AAe2 is Q or deleted or a conservative substitution for Q such as A or N;

AAe3 is M or deleted or a conservative substitution for M such as A;

AAe4 is V or deleted or a conservative substitution for V such as I, L or A;

AAe5 is T or deleted or a conservative substitution for T such as S;

AAe6 is T or deleted or a conservative substitution for T such as S.

It is preferred that at least 1, and preferably 4, of the AAe amino acids be present.

In addition to these peptide sequences per se, ketomethylene- and hydroxyethylene-containing peptides can be employed, as can pharmaceutically acceptable salts of these compounds.

A group of preferred sequences is given in Table 1.

TABLE 1

| Peptide No. | | | Sequence | | | |
|---|---|---|---|---|---|---|
| 6. | C | A T C | E Q I A D S Q H | R S H | R Q M V | (SEQ ID NO: 1) |
| 7. | C | A T C | E Q I A D S Q H | R S H | R Q M | (SEQ ID NO: 2) |
| 8. | C | A T C | E Q I A D S Q H | R S H | R Q | (SEQ ID NO: 3) |
| 9. | C | A T C | E Q I A D S Q H | R S H | R | (SEQ ID NO: 4) |
| 10. | C | A T C | E Q I A D S Q H | R S H | | (SEQ ID NO: 5) |
| 11. | C | A T C | Q I A D S Q H | R S H | R Q M V | (SEQ ID NO: 6) |
| 12. | C | A T C | I A D S Q H | R S H | R Q M V | (SEQ ID NO: 7) |
| 13. | C | A T C | A D S Q H | R S H | R Q M V | (SEQ ID NO: 8) |
| 14. | C | T C | E Q I A D S Q H | R S H | R Q M V | (SEQ ID NO: 9) |
| 15. | C | A C | E Q I A D S Q H | R S H | R Q M V | (SEQ ID NO: 10) |
| 16. | C | A T C | E Q I A D S Q H | R H | R Q M V | (SEQ ID NO: 11) |
| 17. | C | A T C | E Q I A D S Q H | R H | R Q M V | (SEQ ID NO: 12) |
| 18. | Ac—C | A T C | E Q I A D S Q H | R S H | R Q M V | (SEQ ID NO: 13) |
| 19. | Ac—C | A T C | E Q I A D S Q H | R S H | R Q M V—NH$_2$ | (SEQ ID NO: 14) |
| 20. | C | A A C | E Q I A D S Q H | R S H | R Q M V | (SEQ ID NO: 15) |
| 21. | C | A T C | A Q I A D S Q H | R S H | R Q M V | (SEQ ID NO: 16) |
| 22. | C | A T C | E A I A D S Q H | R S H | R Q M V | (SEQ ID NO: 17) |
| 23. | C | A T C | E Q A A D S Q H | R S H | R Q M V | (SEQ ID NO: 18) |
| 24. | C | A T C | E Q I A A S Q H | R S H | R Q M V | (SEQ ID NO: 19) |
| 25. | C | A T C | E Q I A D A Q H | R S H | R Q M V | (SEQ ID NO: 20) |
| 26. | C | A T C | E Q I A D S A H | R S H | R Q M V | (SEQ ID NO: 21) |
| 27. | C | A T C | E Q I A D S Q H | A S H | R Q M V | (SEQ ID NO: 22) |
| 28. | C | A T C | E Q I A D S Q H | R A H | R Q M V | (SEQ ID NO: 23) |
| 29. | C | A T C | E Q I A D S Q H | R S H | A Q M | (SEQ ID NO: 24) |
| 30. | C | A T C | E Q I A D S Q H | R S H | R A M V | (SEQ ID NO: 25) |
| 31. | C | A T C | E Q I A D S Q H | R S H | R Q A V | (SEQ ID NO: 26) |
| 37. | C | A T C | E Q I A D S Q H | R S H | R Q M A | (SEQ ID NO: 28) |
| 38. | C | A T C | E Q I A D S Q H | K S H | R Q M V | (SEQ ID NO: 29) |
| 39. | C | A T C | E Q I A D S Q H | R S H | K Q M V | (SEQ ID NO: 30) |
| 40. | C | A T C | E Q I A D S Q H | K S H | K Q M V | (SEQ ID NO: 31) |
| 41. | C | A S C | E Q I A D S Q H | R S H | R Q M V | (SEQ ID NO: 32) |
| 42. | C | A T C | D Q I A D S Q H | R S H | R Q M V | (SEQ ID NO: 33) |
| 43. | C | A T C | E N I A D S Q H | R S H | R Q M V | (SEQ ID NO: 34) |
| 44. | C | A T C | E Q L A D S Q H | R S H | R Q M V | (SEQ ID NO: 35) |
| 45. | C | A T C | E Q V A D S Q H | R S H | R Q M V | (SEQ ID NO: 36) |
| 46. | C | A T C | E Q I A E S Q H | R S H | R Q M V | (SEQ ID NO: 37) |

TABLE 1-continued

| Peptide No. | | | Sequence | | | | |
|---|---|---|---|---|---|---|---|
| 47. | C | A T C | E Q I A D T Q H | R S H | R Q M V | (SEQ ID NO: 38) |
| 48. | C | A T C | E Q I A D S N H | R S H | R Q M V | (SEQ ID NO: 39) |
| 49. | C | A T C | E Q I A D S Q H | R T H | R Q M V | (SEQ ID NO: 40) |
| 50. | C | A T C | E Q I A D S Q H | R S H | R N M V | (SEQ ID NO: 41) |
| 51. | C | A T C | E Q I A D S Q H | R S H | R Q M L | (SEQ ID NO: 42) |
| 52. | C | A T C | E Q I A D S Q H | R S H | R Q M V | (SEQ ID NO: 43) |
| 53. | C | D—Ala T C | E Q I A D S Q H | R S H | R Q M V | (SEQ ID NO: 44) |
| 54. | C | A T C | E Q I A D S Q H | D—Arg S H | R Q M V | (SEQ ID NO: 45) |
| 55. | C | A T C | E Q I A D S Q H | R S H | D—Arg Q M V | (SEQ ID NO: 46) |
| 56. | C | D—Ala T C | E Q I A D S Q H | D—Arg S H | R Q M V | (SEQ ID NO: 47) |
| 57. | C | D—Ala T C | E Q I A D S Q H | D—Arg S H | D—Arg Q M V | (SEQ ID NO: 48) |
| 58. | C | NMe—Ala T C | E Q I A D S Q H | R S H | R Q M V | (SEQ ID NO: 49) |
| 59. | C | A T C | E Q I A D S Q H | N—MeArg S H | R Q M V | (SEQ ID NO: 50) |
| 60. | C | A T C | E Q I A D S Q H | R S H | N—MeArg Q M V | (SEQ ID NO: 51) |
| 61. | C | NMe—Ala T C | E Q I A D S Q H | NMe—Arg S H | R Q M V | (SEQ ID NO: 52) |
| 62. | C | NMe—Ala T C | E Q I A D S Q H | NMe—Arg S H | NMe—Arg Q M V | (SEQ ID NO: 53) |
| 63. | Ketomethylene- and hydroxyethylene-containing peptides. | | | | | |

[a] Zinc-binding residues are in bold.
[b] Replacement residues are underlined.

One explanation of why these peptides including C1, C2, H, and H2 amino acid residues are so active in that they bind with zinc and constitute a finger called zinc finger which then binds to RNA. FIG. 1 illustrates the configuration of this zinc finger in a peptide (peptide 6) in the native 148–166 region of $M_1$.

Synthesis and Characterization of Peptides

Peptides can be synthesized by solid-phase techniques (Erickson and Merrifield, *The Proteins*, Vol. II., H. Neurath (ed.), Academic Press, Inc., NY, pp. 255–527 (1976)) on a Beckman Model 990C automated peptide synthesizer or a multiple peptide synthesizer (designed by Amrit Judd, P. I. at SRI International, with a capacity to simultaneously synthesize 16 peptides) using commercially available t-BOC amino acids attached to polystyrene resin and t-BOC-protected amino acids with the following side-chain protecting groups: O-benzyl esters for Asp and Glu; O-benzyl ether for Thr and Ser; tosyl for Arg; DNP for His, p-methoxy-benzyl for Cys: o-chlorobenzyloxy-carbonyl for Lys; and 2,6-dichlorobenzyl for Tyr. All couplings can be performed using a 3-molar excess of t-BOC amino acid and dicyclohexylcarbodiimide (DCC) over the number of milliequivalents of amino acid on the resin. In the cases of Asn and Gln, a 3-molar excess of t-BOC-amino acid, DCC, and hydroxybenzotriazole (HOBT) should be used. TFA-$CH_2Cl_2$ (40%) containing 0.1% indole and 10% anisole as scavengers can be used for BOC deprotection. The details of the synthetic cycle are given in Table 2.

TABLE 2

Scheduling of Events for Assembling the Peptide on Resin

| Step | Reagent of Solvent | Time (min) |
|---|---|---|
| 1. | $CH_2Cl_2 \times 3$ | 1.5 |
| 2. | 40% TFA/$CH_2Cl_2$ prewash | 5 |
| 3. | 40% TFA/$CH_2Cl_2$ | 30 |
| 4. | $CH_2Cl_2 \times 6$ | 1.5 |
| 5. | 80% isopropanol/$CH_2Cl_2 \times 3$ | 1.5 |
| 6. | $CH_2Cl_2 \times 3$ | 1.5 |
| 7. | 5% diisopropylethylamine/$CH_2Cl_2 \times 2$ | 10 |
| 8. | $CH_2Cl_2 \times 3$ | 1.5 |
| 9. | coupling; 3-fold excess of t-Boc amino acid in $CH_2Cl_2$:DMF (9:1; v/v) DCC/$CH_2Cl_2$ | 120 |
| 10. | $CH_2Cl_2 \times 3$ | 1.5 |
| 11. | 80% isopropanol/$CH_2Cl_2 \times 3$ | 1.5 |

After completion of the synthesis, the peptides can be cleaved from the resin using anhydrous hydrogen fluoride in the presence of 10% anisole and 1% ethanedithiol, as scavengers, at 4° C. for 1 hr.

The DNP group of His is removed before HF cleavage by treatment with a 20-fold excess of thiophenol (Stewart and Young, *Solid Phase Peptide Synthesis*, 1984, p. 83). The various organic side products can be separated from the peptides by extraction with ether and isolated from the resin by extraction with 50% acetic acid, diluted with water to about 5% and lyophilized. The crude peptides can be purified by HPLC using a 60 cm/20 mm prep. column packed with Vydac 15–20 micron $C_{18}$.

Synthesis of Ketomethylene- and Hydroxyethlyene-Containing Peptidomimetics

There are many synthetic approaches for making ketomethylene-containing peptides. In all cases the initial step requires the synthesis of ketomethylene-containing dipeptide units with appropriate side-chain and amino terminal protecting groups. The method chosen to prepare a particular ketomethylene-containing dipeptide will depend on the nature of the side chains of the dipeptide selected for replacement. The commonly used methods for such syntheses are described by Harbeson and Rich, *J. Med. Chem.* 32, 1378–1392 (1989), Garcia-Lopez et al., *Tetrahedron* 44, 5131–5138 (1988) and 29, 1577–1580 (1988). Johnson and Miller (*Int. J. Peptide Protein Res.* 23, 581–590 (1984)) and Jennings-White and Almquist (*Tetrahedron Lett.* 23, 2533–2534 (1982)). Incorporation of ketomethylene-containing dipeptides into larger peptides will be done by solid-phase synthesis using BOC protection for the amino termini. This method was developed at SRI International by Dr. Ronald Almquist and has been used successfully to prepare peptide mimics containing as many as two ketomethylene-linkages in the same peptide (Almquist, R. G. et al., *J. Med. Chem.* 31, 561 (1988)).

Hydroxyethylene linkages can be synthesized from ketomethylene-containing peptides by simple reduction with sodium borohydride. If desired, stereoselective methods are available for preparing both ketomethylene (Harbeson and Rich 1989, supra) and hydroxyethylene-containing dipeptides (Prasad and Rich, *Tetrahedron Lett.* 31, 1803–1806 (1990)).

The synthesis of a dipeptide mimic can be carried out to give a ketomethylene-containing analog of the most active peptide arrived at on the basis of SAR studies. Scheme 1 describes the synthesis of Arg-Ser ketomethylene that can be used to prepare a dipeptide mimic.

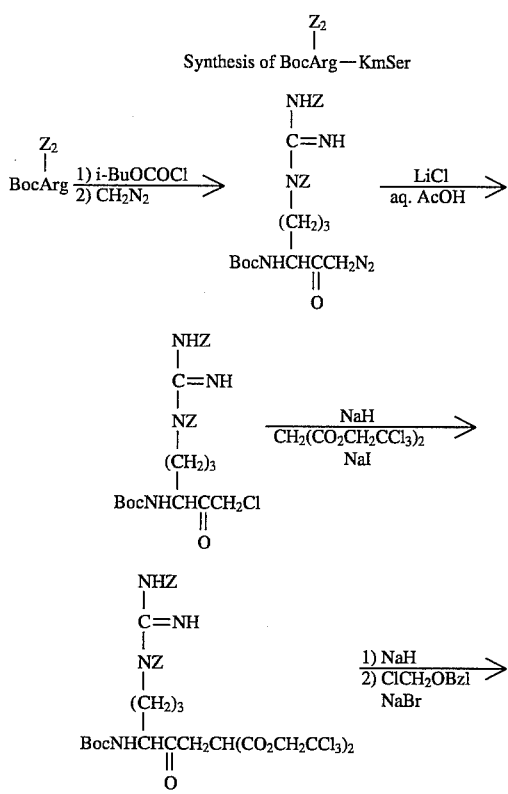

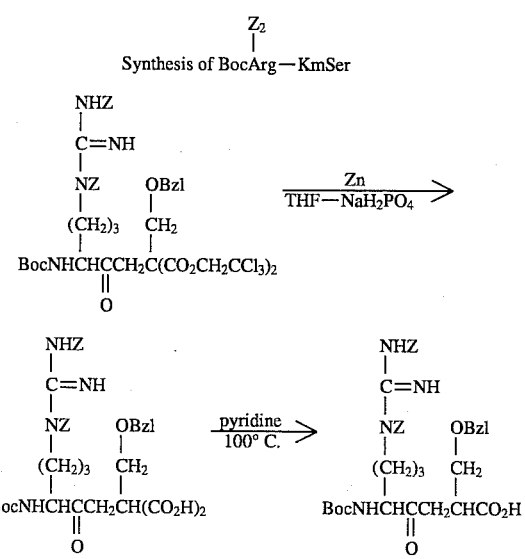

Our experience in synthesizing $Z_3$Arg-KmNle using a similar synthetic route and incorporating it into peptides by solid phase synthesis, showed that the optical center adjacent to the keto-group racemizes during HF cleavage and subsequent aqueous TFA during C18-HPLC purification. Since the serine optical center is also racemic, four diastereomers are obtained with peptides containing arginine ketomethylene dipeptides. One can isolate all of the four diastereomers. Substitution of Arg by Lys or other residues prevents this undesired racemization.

Conversion of ketomethylene-containing peptides to hydroxyethylene derivatives is achieved by treatment of the purified ketomethylene-containing peptide with $NaBH_4$.

Salt Formation. The peptides in free base form may be converted to the acid addition salts by treating with a stoichiometric excess of the appropriate organic or inorganic acid, such as, for example, phosphoric, pyruvic, hydrochloric or sulfuric acid, and the like. Typically, the free base is dissolved in a polar organic solvent such as ethanol or methanol, and the acid added thereto. The temperature is maintained between about 20° C. and 100° C. The resulting acid addition salt precipitates spontaneously or may be brought out of solution with a less polar solvent.

Other pharmaceutically acceptable nontoxic salt derivatives of the peptides of the invention are prepared by treating the free acids with an appropriate amount of pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, isopropanol, butanol, acetone, dioxane or tetrahydrofuran. The molar ratio of peptides of the invention to base used are chosen to provide the ratio desired for any particular salt. For preparing, for example, the calcium salts or magnesium salts, the free acid starting material can be treated with at least one-half molar equivalent of pharmaceutically acceptable base to yield a neutral salt. When the aluminum salts of the peptides of the invention are prepared, at least one-third molar equivalent of the pharmaceutically acceptable base are employed if a neutral salt product is desired.

The salt derivatives of the peptides of the invention can be reconverted to their respective free acids by acidifying said salts with an acid, preferably an inorganic acid, e.g., hydrochloric acid, sulfuric acid, and the like, at temperature of from about 0= C. to about 50° C., preferably at room temperature.

Synthesis of Lipopeptides. Pharmacologically-effective intracellular concentration of small peptides often is achieved by using penetration enhancement. Thus, it is often advantageous to modify the peptide to enhance membrane permeability. To accomplish this one can use either of two strategies. (1) One can incorporate tripalmitoyl-S-glyceryl cysteine ($P_3CSS$) according to the procedure of Deres et al., Nature 342, 561–564 (1989). This modification produces lipophilic peptides; such peptides have been reported to mediate attachment to the cell membrane and internalization into the cytoplasm (id.). (2) One can also derivatize the candidate peptide by adding lipophilic n-alkylamino acid oligomers at the N- or C-terminus. These derivatives have been reported to enhance the cellular uptake of peptides (Toth, I. et al., In Proceedings of the Eleventh American Peptide Symposium, (1990)).

Encapsulation of Peptides into Liposomes. The peptides of the invention can also be encapsulated into liposomes to induce internalization of peptides into cells. Large multilamellar liposomes are prepared from a mixture of dipalmitoylphosphatidyl-choline, cholesterol, and dipalmitoyl phosphatidic acid in a molar ratio of 2.0:1.5:0.2, respectively (Sanchez, Y. et al., Infect. Immun. 30, 728–733 (1980)).

Biological Testing

As will be illustrated in the Example, the peptide identified as Peptide 6 has shown unexpectedly high activity as an inhibitor of viral transcription. One can determine the activity of other candidate peptides by the following methods.

Biological Evaluation. The experimental evaluation of peptides and peptide analogs of the invention is based on the need to obtain compounds with antiviral activity against influenza A major strains representing distinct subtypes and influenza B. Antiviral activity is assessed by the ability of the peptides or peptide analogs to (a) inhibit transcription, (b) bind to RNA, (c) inhibit plaque formation, and (d) cause plaque-size reduction. The candidate peptides are also tested in vivo in mice by subcutaneous administration or intranasal instillation of the candidate peptide and determination of its effect on viral replication. The details of these biological assays are described below.

Growth and Purification of Virus. Influenza virus (A/PR8/34) can be propagated in 10-day-old embryonated eggs (Gallagher, M. et al., *J. Clin. Microbiol.* 20, 89–93 (1984)). It is estimated that 1000 eggs will produce 100 mg of viral protein. Following collection of allantoic fluid from infected eggs and centrifugation at low speed to remove debris, the allantoic fluid preparation is centrifuged at 20,000 rpm for one hour to pellet the virus. The virus is further purified by centrifugation onto the interface of a 30/60% sucrose gradient. Type B influenza virus (B/Lee/40) is grown and purified in a similar way.

Purification of $M_1$. $M_1$ is purified according to an SDS (sodium dodecyl sulfate) gel chromatography technique developed earlier (Bucher 1980, supra; and Bucher, D. J. et al., *Proc. Natl. Acad. Sci. USA* 73, 238–242 (1976)). Purified, pelleted virus is disrupted with 10% SDS with sonication and heating at 56° C. for 15 min and subsequently applied to a Sepharose 6B-CL column. No reducing agent is added in order to maintain disulfide bridges of the hemagglutinin; under non-reducing conditions, $M_1$ is the only viral component that chromatographs with a molecular weight of 25,000. Column fractions are assayed for $M_1$ by SDS gel electrophoresis and pure fractions are pooled. Fractions containing $M_1$ with any impurities are recycled to improve purity. Fractions are concentrated in an Amicon ultrafiltration cell equipped with PM-10 membranes. SDS is removed by several days' dialysis versus multiple changes of distilled water at 4° C. This technique has been used to purify $M_1$ from both types A and B influenza viruses.

Purification of RNA-Transcriptase "Cores". RNA transcriptase cores are prepared according to Rochovansky, O. M., *Virology* 73, 327–338 (1976), as modified by Plotch, J. J. et al., *Cell* 23, 847–858 (1981). Pelleted influenza virus is disrupted by incubation at 31° C. for 25 min in 1 ml of buffer, 0.1M Tris HCl at pH 8.1 containing 0.1M KCl, 5 mm $MgCl_2$, 1.5 mM DTT, 5% glycerol, 1.5% Triton N101 and 1% lysolecithin. The mixture is centrifuged on 30% to 60% (w/v) glycerol gradients in 0.05M Tris HCl at pH 7.8 and 0.15M NaCl at 59,000 rpm for 3 hr at 4° C. in a WS65 rotor. A 1 ml cushion of 70% glycerol underlies the glycerol gradient. Purified viral cores sediment to about the middle of the 30% to 60% glycerol gradient. Use of this protocol in our laboratory resulted in a core preparation with a 21.3-fold increase in specific activity of polymerase as assayed below.

More sensitive assays for transcriptase inhibition are obtained with more highly purified cores prepared as described by Kato, A. et al., *Virus Res.* 3, 115–127 (1985). These authors report that complete removal of $M_1$ from the polymerase complex by phosphocellulose chromatography resulted in a 60-fold increase in transcriptase activity. This procedure requires purification of the cores from CsTFA gradients following centrifugation of the viral lysate for 12 hr at 22,000 rpm in a SW27 rotor. Phosphocellulose chromatography is performed using a 20 ml bed volume with the column pre-equilibrated with 10 mM Tris HCl at pH 7.8, containing 20% glycerol and 1 mM DTT. Fractions containing transcriptase activity are eluted with a 0 to 1M linear NaCl gradient. Rechromatography with a second phosphocellulose column equilibrated with column buffer containing 2% NP40 and elution with a 0 to 1M NaCl linear gradient results in purified RNA polymerase-RNA complex with a transcriptase activity 3000-fold greater in specific activity than the starting virus preparation.

Assay for ApG Primed RNA Polymerase Activity (and its Inhibition). Transcriptase activity is assayed as described by Kato (supra). The assay is conducted for 30 min at 30° C. in a final volume of 0.1 ml. The reaction mixture contains 50 mM Tris HCl (pH 7.8 at 25° C.), 1 mM $MgCl_2$, 100 mM NaCl, and 5 mM DTT with added ApG (250 μM), 200 μM ($^3H$) ATP (approx. $3.0\times10^5$ dpm/nM) and 200 μM each of CTP, GTP and UTP. The reaction is terminated by addition of an equal volume of 10% cold TCA solution. TCA insoluble radioactivity will be collected on GF/C glass filters (Whatman) and counted by liquid scintillation. Purified $M_1$ will serve as the "control" inhibitor. Specificity of the reaction can be verified by use of monoclonal antibodies specific to $M_1$ to reverse inhibition (Hankins 1989, supra) and Bucher et al. 1989, supra).

RNA Binding Activity of $M_1$ and Peptides. Purified $M_1$ and synthetic peptides and peptide analogs are tested for RNA binding activity as described by Ye et al. 1989, supra. Viral RNA is labeled with $^{32}$p by growing influenza virus in MDCK cell monolayers in the presence of phosphate-free minimal essential medium containing $^{32}P_i$. RNA is extracted according to the method of Both and Air, *Eur. J. Biochem.* 96, 363–372 (1970), which includes an incubation with SDS and proteinase K followed by extractions with phenol and chloroform. Peptides or $M_1$ are blotted onto nitrocellulose with the aid of a slot-blot apparatus, washed with a probing Tris buffer containing BSA, Ficoll, EDTA, NaCl, and polyvinylpyrrolidone, followed by probing buffer containing $^{32}$P-labeled viral RNA in a 1:4000 ratio with carrier yeast tRNA (id.). The sheets are then washed several times in probing buffer, dried, and subjected to autoradiography. Blots are quantitated by scanning with a Hoefer densitometer.

Assay for Plaque Inhibition. Peptides and peptide analogs are assessed for their ability to inhibit plaque formation or cause plaque-size reduction of influenza virus on MDCK cell monolayers. A virus inoculum sufficient to produce 30 to 100 plaques is used to infect monolayers in 60 mm plates. A 4 ml overlay of 0.5% agar in minimal essential medium is added. Trypsin (2 µg/ml) is also added to agar, assuming that there is no trypsin-sensitive site in the peptide. Peptides and peptide analogs are added to the agar overlay at varying dilutions. Plates are incubated at 35° C. with 5% $CO_2$ for two to three days and any plaque inhibition or plaque-size reduction is assessed following staining of the plates with crystal violet.

Antiviral Activity of Peptides and Peptide Analogs in Mice. Peptides and peptide analogs are tested for antiviral activity in mice by either of two routes, subcutaneous administration or intranasal instillation. Groups of mice are infected with 100 50% mouse-infective doses of A/PR/8/34 intranasally under light ether anesthesia (Johansson, B. E. et al., *J. Virol.* 63, 1239–1246 (1989)). As the initial protocol, compounds (or placebo) are administered at varying dose levels several hours prior to infection with virus, 6 hr following infection, and on each of the following two days. Amantadine serves as the positive control.

Three days following infection, mice are killed and $10^{-2}$ screening dilutions of homogenized lung suspensions are injected into 10-day-old chicken embryos. Virus-positive lungs are identified by hemagglutination in harvested lung fluids. Antiviral activity is assessed based on reduction in hemagglutination activity over placebo-treated controls.

Antiviral activity of compounds found to be active in mice versus A/Pr/8/34 are tested against other type A influenza virus strains representative of the past decade (H1N1 and H3N2) and type B influenza strains.

Cellular Uptake of Peptides and Peptide Analogs and Localization in the Cell. Peptides and peptide analogs labeled with $^{125}$I can be used to determine the degree of uptake by MDCK cell monolayers and localization within cells. Labeled compounds are added to cell media and placed as overlay on MDCK cell monolayers. The cell monolayers are incubated for 0, 2, 6, and 24 hr at 37° C. The cells are refrigerated, treated with EDTA/trypsin, and washed. Aliquots of cells are saved for total cell counts. Cells are homogenized with a Dounce homogenizer to produce a cytoplasmic extract (Gregorriades, A., *Virology* 79, 449–454 (1977)). Nuclei are prepared by use of NP-40 and sedimentation onto a sucrose cushion as described (id.). $^{125}$I counts are determined individually in whole cells, and in nuclear and cytoplasmic extracts. The chemical form of $^{125}$I is assessed by HPLC to determine the degree of metabolism by cells. First, the cellular extract is analyzed by HPLC to determine if the peptide is intact or has been metabolized. Next, cytoplasmic and nuclear extracts are analyzed to determine the localization of the peptide.

Proteolytic Degradation Studies.

(a) Mouse respiratory tract homogenate. A fresh mouse respiratory tract is homogenized in physiological saline. The peptide is mixed with the homogenate and then shaken in a 37° C. bath. Degradations are monitored by HPLC.

(b) Mouse gastric homogenate. A fresh mouse stomach is homogenized in physiological saline. The peptide is dissolved in 0.1N NaOH and mixed with 0.25% methyl cellosolve in water. The solution is partially neutralized with 0.1N HCl. This solution is mixed with mouse stomach homogenate and incubated at 37° C. Degradation is monitored by HPLC.

(c) Mouse intestinal homogenate. Mouse small intestine is removed immediately after the mouse is sacrificed and minced in Krebs Ringer solution. The peptide sample is mixed with the homogenate and then shaken in a 37° C. bath. Degradations are monitored by HPLC.

Drug Formulations

The peptides of the invention, their salts, and their adducts with liposomes and lipids and the like exhibit antiviral activity and thus find application in antiviral drugs.

These materials may be formulated into dry forms suitable for parenteral (injection, subcutaneous, intramuscular or intravenous), oral, inhalational, or intranasal administration or other systemic administration routes.

Depending on the intended mode of administration, the compositions used may be in the form of solid, semisolid, or liquid dosage forms, such as, for example, tablets, suppositories, pills, capsules, powders, liquids, suspensions, or the like, preferably in unit dosage forms suitable for single administration of precise dosages.

Parenteral administration is generally characterized by injection subcutaneously, intramuscularly, or intravenously. Injectables can be prepared in conventional forms as liquid solutions or as suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of nontoxic auxiliary substances such as wetting or emulsifying agents, pH buffering agents, and the like, such as, for example, sodium acetate, sorbitan monolaurate, triethanolamine oleate, etc.

For solid compositions, conventional nontoxic solid carriers include, for example, pharmaceutical grades of mannitol, lactose, starch, magnesium stearate, sodium saccharin, talcum, cellulose, glucose, sucrose, magnesium carbonate and the like may be used. The active compound as defined above may be formulated as suppositories using, for example, polyalkylene glycols (propylene glycol, for example) as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension suitable for ingestion or injection. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., latest edition. The composition or formulation to be administered will, in any event, contain a quantity of the active compound(s) in an amount effective to alleviate the symptoms of the subject being treated.

For oral administration, it is often preferred to use the peptide derivatives such as those with ketomethylene groups to improve the stability of the peptide in the gastrointestinal tract and enhance the peptide's delivery to the virus itself.

One feature of this invention is the high activity of its compounds. Accordingly, relatively low levels of the compounds are employed, for example doses from about 1 microgram per kilogram of patient body weight to about 5 milligrams per kilogram. Higher or lower amounts can be used if desired.

These drug forms are typically administered as a plurality of doses spread over time so that a complete dosing regimen can include from 1 to 20 serial doses. In any event, an effective dosing amount and pattern—that is, one adequate to have an antiviral effect—should be employed.

EXAMPLES

Example 1

Synthesis of Peptides. Peptides 1–5 not of this invention and peptide 6 of this invention (all found in $M_1$ and all shown in Table 3) were prepared and compared. They were synthesized on a Beckman model 990C automated peptide synthesizer using Merrifield's solid-phase techniques (Erickson and Merrifield in The Proteins, Vol. II, H. Neurath (ed.), Academic Press, Inc., NY, pp. 255–527 (1976)). Crude peptides were purified on a Sephadex LH-20 or by preparative high-pressure liquid chromatography (HPLC) using a reverse-phase Vydac $C_{18}$ column (15 to 20 μm). Purity of the peptide was checked by analytical HPLC and amino acid analysis. All the peptides were at least 99% pure.

For immunological studies, peptides were conjugated to carrier protein keyhole limpet hemocyanin (KLH), bovine serum albumin (BSA), or thyroglobulin by the protocol described by Atassi and coworkers (Atassi, M. Z. et al., *Biochim. Biophys. Acta* 670, 300–302 (1981)).

TABLE 3

Amino Acid Sequences of Peptides Synthesized From M-Protein A/PR/8/34

| Peptide No. | Amino Acid Sequence | |
|---|---|---|
| | 66 | 78 |
| 1. | LTVPSERGLQRRR (SEQ ID NO: 54) | |
| | 83 | 100 |
| 2. | ALNGNGDPNNMDKAVKLY (SEQ ID NO: 55) | |
| | 104 | 118 |
| 3. | KREITFHGAKEISLS (SEQ ID NO: 56) | |

TABLE 3-continued

Amino Acid Sequences of Peptides Synthesized From M-Protein A/PR/8/34

| Peptide No. | Amino Acid Sequence | |
|---|---|---|
| | 152 | 166 |
| 4. | EQIADSQHRSHRQMV (SEQ ID NO: 57) | |
| | 220 | 236 |
| 5. | GTHPSSSAGLKNDLLEN (SEQ ID NO: 58) | |
| | 148 | 166 |
| 6. | CATCEQIADSQHRSHRQMV (SEQ ID NO: 59) | |

Preparation of Virus, $M_1$-Protein and "Cores". a) Propagation and purification of influenza virus. Influenza virus of the A/PR/8/34 strain was propagated in 10-day-old embryonated eggs (Gallagher, M. et al., *J. Clin. Microbiol.* 20, 89–93 (1984)). b) Purification of $M_1$. $M_1$ was purified by sodium dodecyl sulfate (SDS) gel chromatography under non-reducing conditions (Bucher, D. J. et al., *J. Virol.* 36, 586–590 (1980)). Purity was assessed by SDS gel electrophoresis (Gallagher, supra). SDS was removed by exhaustive dialysis against large amounts of distilled water. c) Purification of "cores" with transcriptase activity. The RNA polymerase-RNA complex was purified according to Rochovansky (Rochovansky, O. M., *Virology* 73, 327–338 (1976)) as modified by Plotch and coworkers (Plotch, J. J. et al., *Cell* 23,847–858 (1981)). This procedure resulted in a core preparation with 21.3-fold increase in specific activity.

Virus Transcriptase Assay. Transcriptase activity was assayed according to the procedure of Kato and coworkers (Kato, A. et al., *Virus Res.* 3, 115–127 (1985)).

Figure 2:
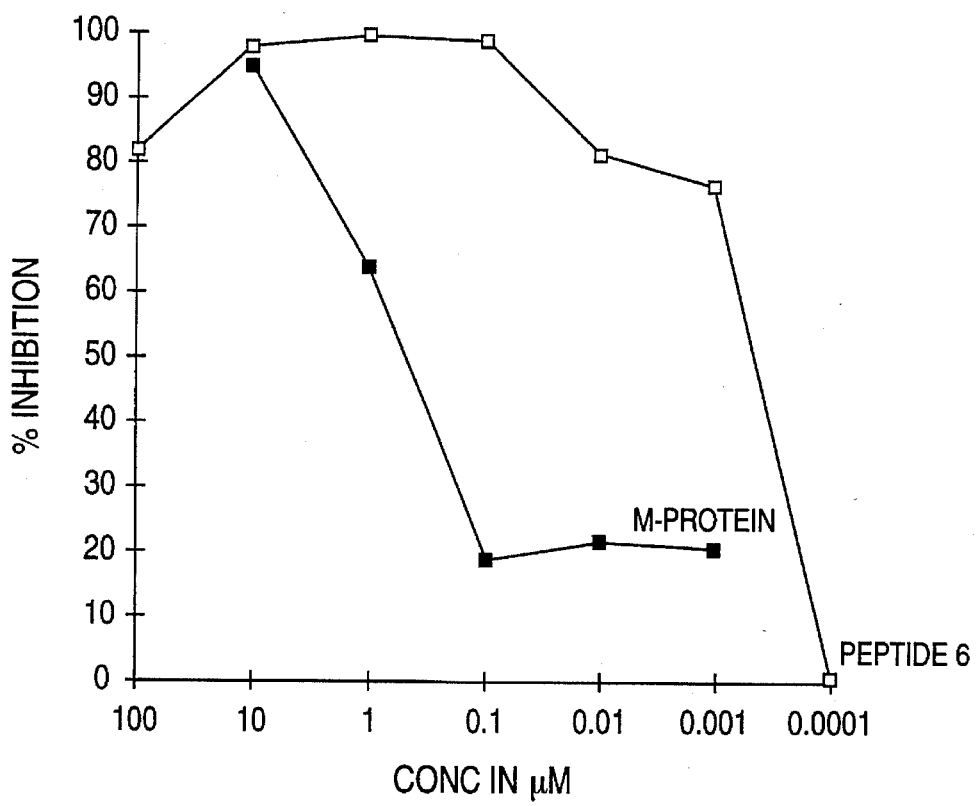
FIG. 2 is a graph comparing the polymerase inhibition activity of $M_1$ with that of a peptide of this invention.

Results and Discussion. Peptide 1 exhibited 35% inhibition at 50 μM concentration whereas Peptide 4 exhibited 38% inhibition at 50 nM (Table 4). Inhibitory activity of M-protein is shown in FIG. 2 and Table 5. Peptides 2, 3, and 5 exhibited enhancement of polymerase activity (Table 4). These peptides in our previous studies (Bucher, M. et al., 1989, supra) were identified as being from the immunodominant regions (id.)

Peptide 6, which contains a complete zinc finger motif, was found to be much more active than the $M_1$ protein itself. 50% inhibition in the case of $M_1$ protein was between 1 μM and 0.1 μM whereas in the case of the peptide it was in the picomolar range (Table 6, FIG. 2).

Our results indicate that we have identified a fragment from $M_1$ sequence that can inhibit transcription of influenza virus ribonucleoprotein completely and this inhibition of transcription is in a dose-dependent manner. Thus this peptide has great potential in the development of an antiviral drug for influenza. In addition, the peptide could have antiviral activity against the negative-strand viruses indicated.

TABLE 4

| INHIBITION OF POLYMERASE BY PEPTIDES | | | | | | |
|---|---|---|---|---|---|---|
| Peptide Concentration | Molar Concentration | % Inhibition | | | | |
| (μg/100 μl) | (μM) | Peptide 1 | Peptide 2 | Peptide 3 | Peptide 4 | Peptide 5 |
| 10 | 50 | 35 | −13* | −30* | 32 | −30* |
| 1 | 5 | 9 | −20* | −9* | 23 | 1 |

TABLE 4-continued

INHIBITION OF POLYMERASE BY PEPTIDES

| Peptide Concentration (μg/100 μl) | Molar Concentration (μM) | % Inhibition | | | | |
|---|---|---|---|---|---|---|
| | | Peptide 1 | Peptide 2 | Peptide 3 | Peptide 4 | Peptide 5 |
| 0.1 | 0.5 | 2 | −10* | 8 | 22 | 14 |
| 0.01 | 0.05 | 3 | −37* | 9 | 38 | 16 |

*enhancement

TABLE 5

INHIBITION OF POLYMERASE BY M-PROTEIN

| M-Protein Concentration (μg/100 μl) | Molar Concentration (μM) | % Inhibition |
|---|---|---|
| 25 | 10 | 95 |
| 2.5 | 1 | 64 |
| 0.25 | 0.1 | 19 |
| 0.025 | 0.01 | 22 |
| 0.0025 | 0.001 | 21 |

TABLE 6

INHIBITION OF POLYMERASE BY PEPTIDE 6 (148–166)

| Molar Concentration (μM) | % Inhibition | |
|---|---|---|
| | M-Protein | Peptide 6 (148–166) |
| 100 | ND | 81 |
| 10 | 95 | 98 |
| 1 | 64 | >100 |
| .100 | 19 | 99 |
| .010 | 22 | 82 |
| .001 | 21 | 77 |

Example 2

Peptide 6 is formulated into an injectable liquid drug form by dissolving 100 micrograms of 6 per milliliter in injectable saline. This solution is packaged in syringes for injection.

Example 3

Peptide 6 is incorporated into liposomes. Multilaminar lysosomes are prepared from dipalmitoylphosphatidylcholine, cholesterol and phosphatidic acid (Sigma Chemical Co., St. Louis, Mo.) in molar ratios of 1:1.5:0.2, respectively. A dried film of this lipid mixture is then formed and swollen with a solution of peptide 6. As a comparison, this is repeated with $C^{14}$-labeled peptide 6 to determine the amount of peptide entrapped in the liposome material. The materials are repeatedly washed and centrifuged at 18,000 rpm to remove nonentrapped material. The material is then suspended in injectable saline so as to deliver effective doses of protein 6 in the 10 to 1,000 microgram range. In this form, the liposome promotes passage of the peptide into viral particles.

Example 4

Peptide 6 is condensed with α-amino acids having long alkyl side-chains—the so-called fatty amino acids. These materials are coupled through the N or C end of the peptide using a simple amide or ester bond. The fatty amino acids employed are α-amino—C9 to C19 linear alkyl acids or biodegradable oligoalkylpeptides linked through amide bonds to one another with from 9 to 19 carbons in each of the alkyl peptides. (See Toth et al., Eleventh American Peptide Symposium, supra.)

These condensations give rise to a plurality of different forms of protein 6, each of which contains a linear alkyl group suitable for promoting the transport of the peptide into viral particles. Thus, when the material is formulated into an injectable drug (10–1,000 μg/kg dose level), it is increasingly effective.

Example 5

Peptide 6 is synthesized by inserting a ketomethylene group in place of an amino acid at 162–166. This yields a material of increased gastrointestinal tract stability. It is formulated into an oral dosage form as follows:

| | |
|---|---|
| peptide | 30 mg |
| cornstarch | 115 mg |
| lactose | 150 mg |
| magnesium stearate | 5 mg |

These materials are mixed and pressed into tablets for oral administration.

Example 6

Other peptides included in Table 1 and analogs made with conservative substitutions and deletions are made and formulated into drug forms, with and without liposome and/or "fatty amino acid" modification. These materials are then tested as antiviral agents following the protocols set forth herein.

---

What is claimed is:

1. A peptide having antiviral activity against influenza viruses by reason of its ability to inhibit influenza transcription, said peptide having the amino acid sequence CATCEQIADSQHRSHRQMV (SEQ. ID. No. 1).

2. A composition comprising a peptide of claim 1 encapsulated within a liposome.

3. A lipopeptide comprising a peptide of claim 1 coupled to a lipid.

4. A ketomethylene peptide derivative comprising the peptide of claim 1 containing at least one ketomethylene substituent.

5. The peptide of claim 1 wherein the 166 V residue is deleted.

6. The peptide of claim 1 wherein the 166 V and the 165 M residues are deleted.

7. The peptide of claim 1 wherein the 166 V, the 165 M and the 164 Q residues are deleted.

8. The peptide of claim 1 wherein the 166 V, the 165 M, the 164 Q and the 163 R residues are deleted.

9. The peptide of claims 1, 5, 6, 7 or 8 wherein the amino acids Arg and Ala independently may be D amino acids.

10. An antiviral pharmaceutical formulation comprising the peptide of claim 1 in a pharmaceutically acceptable carrier.

11. An antiviral pharmaceutical formulation comprising the peptide of claim 5 in a pharmaceutically acceptable carrier.

12. An antiviral pharmaceutical formulation comprising the peptide of claim 6 in a pharmaceutically acceptable carrier.

13. An antiviral pharmaceutical formulation comprising the peptide of claim 7 in a pharmaceutically acceptable carrier.

14. An antiviral pharmaceutical formulation comprising the peptide of claim 8 in a pharmaceutically acceptable carrier.

* * * * *